(12) United States Patent
Yodfat et al.

(10) Patent No.: US 8,337,486 B2
(45) Date of Patent: Dec. 25, 2012

(54) ENERGY SUPPLY FOR FLUID DISPENSING DEVICE

(75) Inventors: Ofer Yodfat, Maccabim-Reut (IL); Avraham Neta, Gilon (IL); Avihoo Keret, Kfar Vradim (IL)

(73) Assignee: Medingo Ltd., Yoqneam Illit (IL)

( * ) Notice: Subject to any disclaimer, the term of this patent is extended or adjusted under 35 U.S.C. 154(b) by 88 days.

(21) Appl. No.: 12/452,762

(22) PCT Filed: Jul. 20, 2008

(86) PCT No.: PCT/IL2008/000999
§ 371 (c)(1),
(2), (4) Date: Apr. 8, 2010

(87) PCT Pub. No.: WO2009/013734
PCT Pub. Date: Jan. 29, 2009

(65) Prior Publication Data
US 2010/0191078 A1   Jul. 29, 2010

Related U.S. Application Data

(60) Provisional application No. 60/961,528, filed on Jul. 20, 2007, provisional application No. 60/961,484, filed on Jul. 20, 2007, provisional application No. 60/961,382, filed on Jul. 20, 2007.

(51) Int. Cl.
*A61K 9/22* (2006.01)
*A61M 31/00* (2006.01)
*A61M 5/00* (2006.01)
*A61M 1/00* (2006.01)

(52) U.S. Cl. ........ 604/890.1; 604/67; 604/151; 604/244
(58) Field of Classification Search ............. 604/65–67, 604/122, 131, 151, 244, 890.1
See application file for complete search history.

(56) References Cited

U.S. PATENT DOCUMENTS
3,631,847 A   1/1972   Hobbs, II
(Continued)

FOREIGN PATENT DOCUMENTS
CN   2919644 Y   7/2007
(Continued)

OTHER PUBLICATIONS

International Search Report & Written Opinion for PCT Application No. PCT/IL2008/000999, mailed May 15, 2009.
(Continued)

*Primary Examiner* — Victoria P Shumate
(74) *Attorney, Agent, or Firm* — Mintz Levin Cohn Ferris Glovsky and Popeo, P.C.

(57) ABSTRACT

Disclosed is a portable fluid dispensing device for infusing a fluid into the body of a user and/or for sensing an analyte within the body. The device includes at least one housing to retain a source of energy to energize the device, the source of energy comprising at least one electrochemical cell to produce electrical energy upon exposure of the cell to air, and a seal to prevent exposure of the at least one cell to air when the source of energy is not in use and to enable exposure of the at least one cell to air prior to energizing the device with the source of energy. The at least one housing includes an opening to provide access to the seal to enable actuation of the seal to control exposure of the at least one cell to air.

24 Claims, 14 Drawing Sheets

U.S. PATENT DOCUMENTS

| | | |
|---|---|---|
| 3,770,607 A | 11/1973 | Williams |
| 3,771,694 A | 11/1973 | Kaminski |
| 3,953,566 A | 4/1976 | Gore |
| 4,030,495 A | 6/1977 | Virag |
| 4,194,041 A | 3/1980 | Gore et al. |
| 4,313,439 A | 2/1982 | Babb et al. |
| 4,429,000 A | 1/1984 | Naka et al. |
| 4,498,843 A | 2/1985 | Schneider et al. |
| 4,544,369 A | 10/1985 | Skakoon et al. |
| 4,560,611 A | 12/1985 | Naka et al. |
| 4,657,486 A | 4/1987 | Stempfle et al. |
| 4,679,562 A | 7/1987 | Luksha |
| 4,734,092 A | 3/1988 | Millerd |
| 4,846,797 A | 7/1989 | Howson et al. |
| 4,902,278 A | 2/1990 | Maget et al. |
| 5,352,513 A | 10/1994 | Mrozinski et al. |
| 5,390,671 A | 2/1995 | Lord et al. |
| 5,460,603 A | 10/1995 | DeSantis |
| 5,591,541 A | 1/1997 | Oltman |
| 5,607,796 A | 3/1997 | Jacus et al. |
| 5,658,356 A | 8/1997 | Burns |
| 5,662,717 A | 9/1997 | Burns |
| 5,688,864 A | 11/1997 | Goodwin |
| 5,733,676 A | 3/1998 | Dopp et al. |
| 5,804,327 A | 9/1998 | Oltman |
| 5,904,998 A | 5/1999 | Dopp et al. |
| 5,928,194 A | 7/1999 | Maget |
| 5,938,640 A * | 8/1999 | Maget et al. .................. 604/145 |
| 5,957,895 A | 9/1999 | Sage et al. |
| 5,973,055 A | 10/1999 | Michaud et al. |
| 5,985,475 A | 11/1999 | Reynolds et al. |
| 6,143,164 A | 11/2000 | Heller et al. |
| 6,485,461 B1 | 11/2002 | Mason et al. |
| 6,589,229 B1 | 7/2003 | Connelly et al. |
| 6,638,610 B1 | 10/2003 | Yao |
| 6,676,993 B2 | 1/2004 | Klare |
| 6,723,072 B2 | 4/2004 | Flaherty et al. |
| 6,740,059 B2 | 5/2004 | Flaherty |
| 6,743,516 B2 | 6/2004 | Murphy et al. |
| 6,811,884 B2 | 11/2004 | Goodwin et al. |
| 6,854,603 B2 | 2/2005 | Klare |
| 7,083,849 B1 | 8/2006 | Albrecht et al. |
| 7,144,384 B2 | 12/2006 | Gorman et al. |
| 2003/0161744 A1 | 8/2003 | Vilks et al. |
| 2005/0177108 A1 | 8/2005 | Paul et al. |
| 2006/0184154 A1 | 8/2006 | Moberg et al. |
| 2007/0073235 A1 | 3/2007 | Estes et al. |
| 2007/0106218 A1 | 5/2007 | Yodfat et al. |
| 2007/0191702 A1 | 8/2007 | Yodfat et al. |
| 2007/0255198 A1 * | 11/2007 | Leong et al. .................. 604/65 |
| 2008/0051716 A1 * | 2/2008 | Stutz .............................. 604/151 |
| 2008/0102119 A1 * | 5/2008 | Grovender et al. ........... 424/473 |
| 2008/0125701 A1 * | 5/2008 | Moberg et al. .................. 604/67 |
| 2008/0255516 A1 | 10/2008 | Yodfat et al. |
| 2008/0269575 A1 | 10/2008 | Iddan |
| 2008/0294142 A1 * | 11/2008 | Patel et al. .................... 604/506 |
| 2010/0121306 A1 | 5/2010 | Yodfat et al. |
| 2010/0130932 A1 | 5/2010 | Yodfat et al. |
| 2010/0191078 A1 | 7/2010 | Yodfat et al. |
| 2010/0198187 A1 | 8/2010 | Yodfat et al. |
| 2010/0217230 A1 | 8/2010 | Yodfat et al. |
| 2010/0241086 A1 | 9/2010 | Yodfat et al. |
| 2010/0298764 A1 | 11/2010 | Yodfat et al. |

FOREIGN PATENT DOCUMENTS

| | | |
|---|---|---|
| WO | WO-2005082436 A1 | 9/2005 |
| WO | WO-2007037979 A2 | 4/2007 |
| WO | WO-2007045644 A1 | 4/2007 |
| WO | WO-2008139458 A2 | 11/2008 |
| WO | WO-2009125398 | 10/2009 |

OTHER PUBLICATIONS

U.S. Appl. No. 12/452,764, filed Apr. 7, 2010.

* cited by examiner

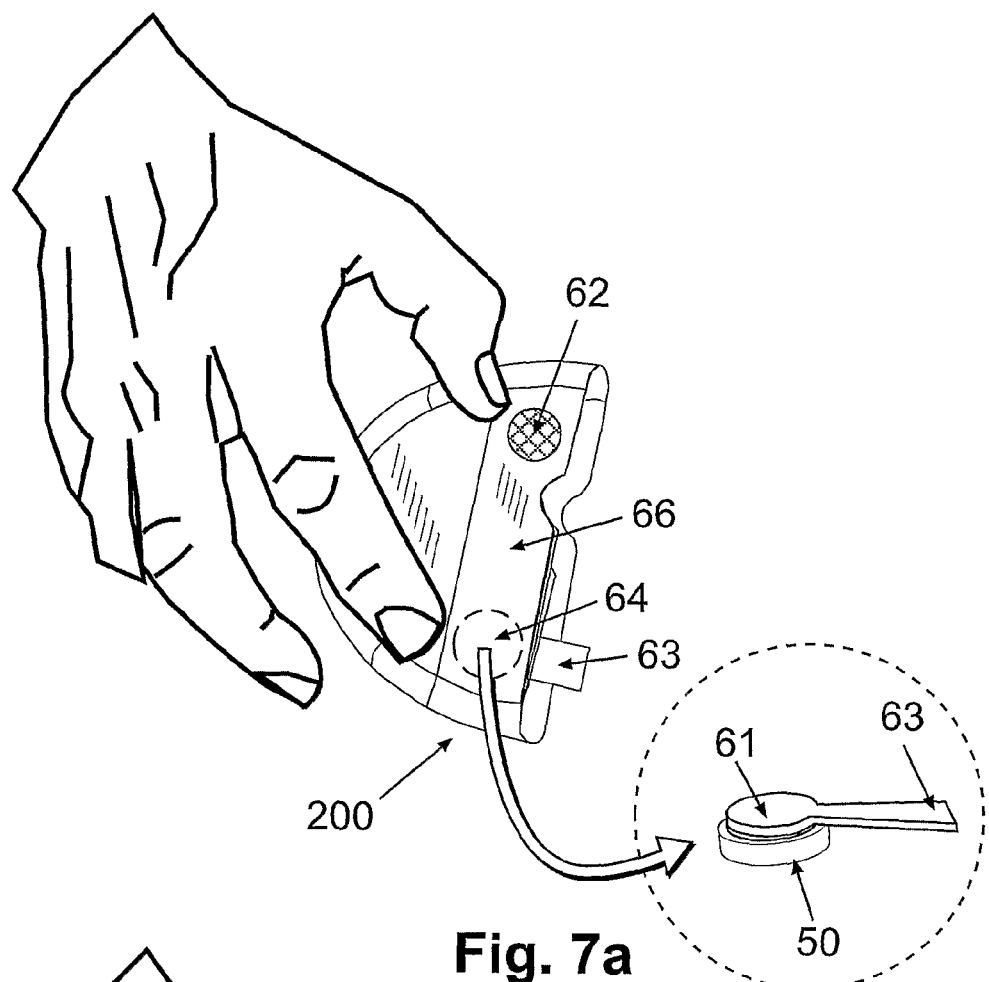
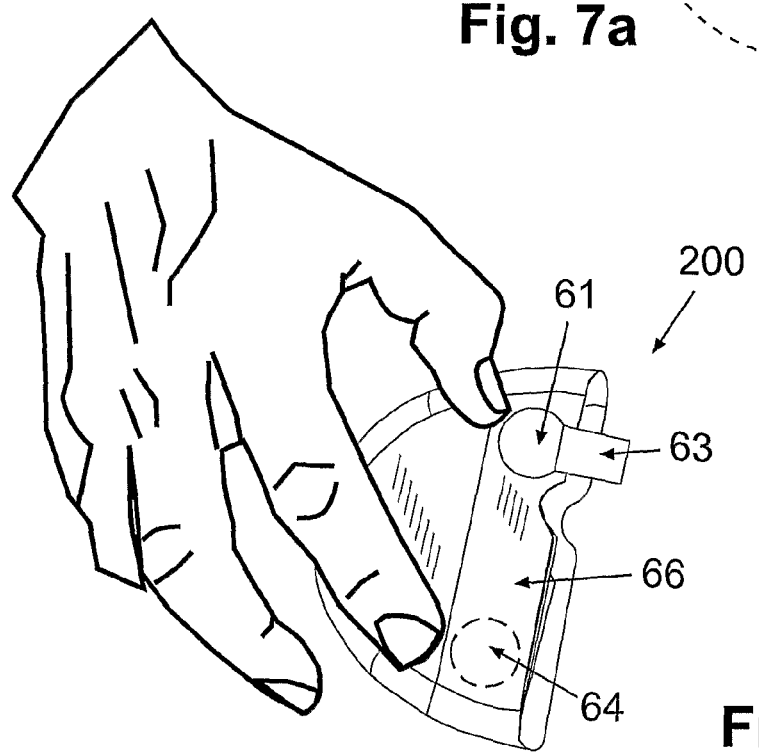
Fig. 7a
Fig. 7b

ENERGY SUPPLY FOR FLUID DISPENSING DEVICE

CROSS-REFERENCE TO RELATED APPLICATIONS

The present application is a 35 U.S.C. § 371 national stage entry of PCT/IL2008/000999, which has an international filing date of 20 Jul. 2008 and claims priority to U.S. Provisional Patent Application Nos. 60/961,528, 60/961,484 and 60/961,382, all of which were filed in the U.S. Patent & Trademark Office on 20 Jul. 2007. The present application incorporates herein by reference the disclosure of each of the above-referenced applications in its entirety.

BACKGROUND OF THE INVENTION

1. Field of the Invention

Embodiments of the present disclosure relate generally to a system, a device and a method for sustained medical infusion of fluids and/or continuous monitoring of body analyte. More particularly, the present disclosure is related to a portable infusion patch-like device securable to the skin that, optionally, can also continuously monitor body analytes. In some embodiments, a multi-component fluid dispensing and/or bodily analytes monitoring device is provided that is powered by a miniature highly efficient energy supply source.

2. Background of Invention

Medical treatment of several illnesses requires continuous drug infusion into various body compartments, such as subcutaneous and intra-venous injections. For example, diabetes mellitus patients require the administration of varying amounts of insulin throughout the day to control their blood glucose levels. In recent years, ambulatory portable insulin infusion pumps have emerged as superior alternatives to multiple daily injections of insulin by syringe. These pumps, which deliver insulin at continuous basal rates as well as in bolus volumes, were developed to liberate patients from repeated self-administered injections, and to enable them to maintain a near-normal daily routine. Other examples of treatments based on the use of infusion pumps are treatments to treat post surgery pain that require relief by medication (e.g., opium derivatives). These drugs may be locally delivered to the subcutaneous tissue surrounding the incision scar to thus avoid systemic side effects of oral or intravenous administered analgesics. Other examples for applications of such pumps include using these pumps with cancer patients that require continuous delivery of chemotherapy medications via an open vein access port.

First generation of portable insulin pumps were "pager like" devices with a reservoir contained within a device housing. A long tube delivered insulin from the pump attached, for example, to a patient's belt to a remote insertion site. The reservoir, delivery tube and the hypodermic cannula were altogether named the "infusion set". The recommendation for infusion set replacement was every 2-3 days to avoid local infection at the cannula insertion site. However, most diabetes pump users extended this period until reservoir emptying, which sometimes occurred up to 7 days after the initial use. Such devices are disclosed, for example, in U.S. Pat. Nos. 3,631,847, 3,771,694, 4,657,486 and 4,544,369, the contents of all of which are hereby incorporated by reference in their entireties. These devices represent a significant improvement over the use multiple daily injections, but suffer from drawbacks, among which are the devices' relative large size and weight. The main factor contributing to the devices' heaviness and bulk was their use of relatively large driving mechanism and large sized batteries (e.g., of AA-type, or AAA-type) required to meet the high energy demands of the motor, screen, alarms and other components of the devices.

These uncomfortable, bulky devices with long tubes are rejected by the majority of diabetic insulin users because they disturb their regular activities, e.g., sport activities such as swimming. To avoid the tubing limitations, a new concept of a second generation was proposed. The new concept included a remote controlled, skin securable (e.g., adherable) device with a housing having a bottom surface adapted for contact with the patient's skin, with a reservoir contained within the housing, and with an injection needle adapted for fluid communication with the reservoir. These skin-securable devices are designed to be replaced every 2-3 days similarly to the currently available pump infusion sets. However, most patients prefer to extend this period until reservoir emptying. This paradigm was described in U.S. Pat. Nos. 4,498,843, 5,957,895, 6,589,229, 6,740,059, 6,723,072, and 6,485,461, the contents of which are hereby incorporated by reference in their entireties. These second generation skin securable devices have two drawbacks. First, the single piece device has to be disposed of every three (3) days with its all expensive components (electronics, driving mechanism, etc.). Second, a $2^{nd}$ generation remote controlled skin-securable device is generally heavy and bulky, which is a drawback because the device is directly attached to the patient's skin and remains in place for at least three (3) days. One of the reasons for the large size and heavy weight is the size and number of batteries that supply energy for maintaining a communication link between the skin securable device and the remote control unit, in addition to supplying energy to the energy-consuming components of the devices, such as the motor, display device, alarm, etc.

In U.S. Pat. No. 7,144,384, the contents of which are hereby incorporated by reference in its entirety, a skin adherable device is disclosed. A large portion of the entire volume of this device is occupied by the batteries. In one embodiment, four watch (button) batteries are needed to meet the dispenser energy requirements. The plane of the four button batteries is positioned perpendicularly to the longitudinal axis of the device and consequently the device is relatively thick (18 mm) and bulky. Moreover, because the energy requirements of the device are high, these heavy and bulky batteries last for only three (3) days forcing the user to dispose of the device after three (3) days.

A watch battery or button cell is a small form-factor battery designed for use in wrist watches, pocket calculators, hearing aids, and similar compact portable electronics products. The main advantage of watch batteries is their size, particularly their thickness. Unlike AA or even AAA cylindrical shape batteries, having diameters of at least 10 mm, watch batteries are flat, usually having a thickness of 3-5 mm. A watch battery typically includes a single cell with nominal voltage between 1.5 and 3 volts. Common anode materials include zinc or lithium, and common cathode materials include manganese dioxide, silver oxide, and carbon monofluoride (or copper oxide). The cylindrical outer casing of these types of batteries forms part of the positive (+) terminal. The "C" type 3-V lithium cells and the "S" type 1.5 volt silver oxide cells are the most commonly used watch batteries.

In U.S. patent application Ser. No. 11/397,115, entitled "Systems and methods for sustained medical infusion and devices related thereto" (published as U.S. Publication No. 2007/0106218), and in U.S. provisional application No. 61/123,509, entitled "Systems, devices and methods for fluid delivery", the contents of which are hereby incorporated by reference in their entireties, a so-called third generation device was described that includes a remote controlled skin adherable dispensing patch having reusable and disposable parts. In some embodiments of these dispensing devices, button batteries residing within the disposable part of a dispensing device are used. Such third generation device described is relatively thin (e.g., a thickness of not more than 15 mm) and meets all energy requirements for the entire usage duration of the device, e.g., more than three days.

The prior art also describes continuous glucose monitors (see, for example, U.S. Pat. Nos. 5,390,671 and 6,143,164, the contents of which are hereby incorporated by reference in their entireties). These devices monitor glucose levels in the subcutaneous compartment of a patient's body. U.S. patent applications Ser. Nos. 11/706,606, 11/989,665 and 11/989,678, the contents of all which are hereby incorporated by reference in their entireties, describe a dual function patch-like fluid dispensing device that dispenses fluids and continuously monitors body analytes (e.g., insulin dispensing and glucose monitoring). In some of the disclosed embodiments of such dual function dispensing device, a closed loop system is described in which insulin was delivered according to certain glucose levels. In some embodiments of such disclosure, the dual function patch is composed of reusable and disposable parts, where, for example, the batteries reside within the disposable part. Similar to the single-piece "stand alone" dispensing device, this dual function device is relatively thin (thickness being not more than 15 mm) and meets all energy requirements for the entire usage duration, e.g., for more than 3 days.

SUMMARY OF THE INVENTION

In some embodiments of the present disclosure, a miniature and thin, portable, programmable fluid dispensing device (hereafter a "dispensing patch") is disclosed that has a minimal space for an energy supply cell which meets the energy requirements of the device for at least a three-day operation period.

In some embodiments, a miniature and thin (e.g., less than 15 min) portable device for continuous monitoring of glucose is provided that contains a minimal space for an energy supply cell and meets the energy requirements of the device for at least a three-day operation period. The continuous monitoring device can be incorporated within the dispensing device, thus providing it with both sensing and dispensing capabilities. In some embodiments, the device can dispense insulin according to monitored glucose levels within a closed loop system.

In some embodiments, a simple and inexpensive dispensing patch that is composed of two parts, a disposable part and a reusable part, is provided. After connecting the reusable and disposable parts, the assembled device has a thin profile with a relatively small footprint.

In some embodiments, a dispensing patch composed of two parts, a disposable part and a reusable part, which delivers fluid into the body of a patient is provided. An energy supply cell is contained within the disposable part and thus there is no need for any battery replacements. Thus, the user does not have to handle the batteries and needs not worry about battery replacement.

In some embodiments, a dispensing patch composed of two parts, a disposable part and a reusable part, that delivers fluid into the body of a patient is provided. The disposable part contains an energy supply cell (e.g., a battery). The disposable part containing the energy supply cell can be disposed in any type trash receptacle, including regular home disposal systems, thus avoiding the use and maintenance of cumbersome toxic waste/biohazards containers.

The present disclosure describes a miniature and thin (e.g., not more than about 20 mm and generally less than 15 mm) portable programmable fluid dispensing patch defining a space of, in some embodiments, less than 3 $cm^3$ for an energy supply cell. More particularly, the disclosure describes a small, low cost, portable dispensing patch comprising a disposable part and a reusable part. The power source is, in some embodiments, contained in the disposable part and includes one or more metal/air batteries. The metal/air battery may include a zinc/air button type battery.

In some embodiments, zinc/air batteries are the energy source for the dispensing patch because they are thin and have high specific energy density (i.e., such batteries are configured to store large amounts of charge relative to their weight and/or volume) to meet dispenser requirements. When batteries are contained within the disposable part they can be disposed of approximately every three (3) days (e.g., by placing it in a non-biohazard garbage can). The production cost of the disposable part is a key issue in product profitability and thus a low cost of the zinc/air batteries is another advantage for their use. However, other battery types providing similar advantages may also be used in the device as described herein in the present disclosure.

In some embodiments, a single zinc/air battery is provided within the disposable part. The flat portion of the battery is aligned with the disposable part housing thus enabling a very thin device configuration. Optionally the electrical connectors are soldered directly to the battery cathode. This soldering avoids inadvertent disconnections from the battery.

A zinc/air battery requires oxygen for operation, and therefore its cathode should be insulated before activation. Thus, in some embodiments, the device includes the following features:

- The battery is positioned in the device such that the cathode insulation cover (or seal) can be removed. In the case of a two part device, the cover may be removed from the battery in the disposable part before the parts are paired.
- A vent is provided in the device housing to enable free air movement. The vent enables directing air (i.e., air ingress) to enter the device housing and come in contact with the zinc/air cell(s). The vent may include a semi-permeable membrane to prevent, for example, water penetration.

Since the power output (e.g., wattage, current and/or voltage) of zinc-air batteries is insufficient for activation of the dispensing patch's larger power-consuming electrical components, a high capacity capacitor (e.g., at least 100 mF) may be provided to meet momentary power/current requirements.

In some of the embodiments of the present disclosure, a method to meet the power and current requirements of the device's electrical components is disclosed. Thus, in some embodiments, the present disclosure provides a thin (e.g., the smallest dimension is less than about 15 mm) dispensing patch that contains at least one button (watch) battery, such as a silver oxide battery.

In some embodiments, a fluid dispensing patch is provided that contains a monitor for continuous monitoring of analyte. In some embodiments, the fluid dispending patch is an insulin dispensing patch. In some embodiments, the analyte that is monitored by the device is glucose. In some embodiments, the device contains at least one button battery. In some embodiments, the device can dispense insulin according to monitored glucose levels, thus implementing a closed loop system.

In some embodiments, a thin (e.g., 15 mm) dispensing patch is provided that contains at least one zinc/air battery. The disclosure also describes a method to enable oxygen entry into the device housing.

In some embodiments, a dispensing patch composed of two parts, a disposable part and a reusable part, is provided. A zinc/air battery may be placed within the disposable part (e.g., during manufacturing of the part) and thus battery replacement is not necessary. The zinc/air battery may include a seal that can be removed before, or after, parts pairing.

In one aspect, a portable fluid dispensing device for infusing a fluid into the body of a user and/or for sensing an analyte within the body is disclosed. The device includes at least one housing to retain a source of energy to energize the device, the source of energy comprising at least one electrochemical cell to produce electrical energy upon exposure of the cell to air, and a seal to prevent exposure of the at least one cell to air when the source of energy is not in use and to enable exposure of the at least one cell to air prior to energizing the device with the source of energy. The at least one housing includes an opening to provide access to the seal to enable actuation of the seal to control exposure of the at least one cell to air.

Embodiments of the device may include one or more of the following features.

The at least one housing of the device may be adapted to provide access to a tab of the seal to enable removal of the seal to cause the exposure of the at least one cell to the air.

The device may further include a sensor module for sensing a bodily analyte level.

The device may further include the source of energy held in the at least one housing.

The seal may be secured to at least one surface of the source of energy through which air comes in contact with air-reactive parts of the source of energy. The seal may include a removable tab such that upon removal of the tab, the at least one cell of the source of energy is exposed to air.

The at least one cell may includes at least one Zinc-Air cell.

The source of energy may be configured as a button battery.

The at least one housing may further include at least one air vent opening to enable air to be delivered to the source of energy, and a semi-permeable membrane placed in the at least one air vent opening, the semi-permeable membrane configured to enable entry of air into the at least one housing and to substantially prevent entry of at least some other materials into the at least one housing. The at least some other materials may include at least one of, for example, water and/or other liquids.

The device may further include a second seal to prevent entry of air into the at least one housing through the at least one air vent opening when the device is not in operation. The second seal may cover the semi-permeable membrane to prevent entry of air into the at least one housing through the at least one air vent opening.

The at least one housing may include a dedicated energy source cover to retain at least the energy source, and at least one second housing, the at least one second housing configured to receive and retain the dedicated energy source cover.

The at least one housing may include a reusable part housing including a driving mechanism and a processor, and a disposable part housing including a reservoir to hold a therapeutic fluid and the source of energy. The source of energy may provide energy to the driving mechanism and/or processor.

The disposable part may include a housing manufactured in a manner such that a portion of the housing retaining the source of energy is integrally formed around the source of energy source such that the source of energy cannot be removed.

The source of energy may have a volume of less than about 3 $cm^3$.

The at least one housing may have a thickness of less than about 15 mm.

In another aspect, a portable fluid dispensing device for infusing a fluid into the body of a user is disclosed. The device includes at least one housing to retain at least a source of energy to energize the device, a pump to deliver a therapeutic fluid to the user, a driving mechanism to activate the pump, a processor to control the pump and/or driving mechanisms operations, and a capacitor to temporary store charge from the source of energy during a first time interval and discharge the stored charge to activate the driving mechanism during a second time interval. The first time interval is longer than the second time interval.

Embodiments of the device may include any of the features of the first device described above, as well as any one of the following features.

The first time interval may be at least 20 times longer than the second time interval.

The first time interval may be about 50 times longer than the second time interval.

The first time interval may overlap, at least in part, the second time interval.

The device may further include the source of energy.

In a further aspect, a portable fluid dispensing device for infusing a fluid into the body of a user and/or for sensing an analyte within the body is disclosed. The device includes a source of energy to energize the device, the source of energy comprising at least one electrochemical cell to produce electrical energy upon exposure of the cell to air. The device also includes at least one housing to retain the source of energy, and a seal to prevent exposure of the at least one cell to air when the source of energy is not in use and to enable exposure of the at least one cell to air prior to energizing the device with the said source of energy. The at least one housing is manufactured in a manner such that a portion of the at least one housing retaining the source of energy is integrally formed around the energy source such that the energy source cannot be removed.

Embodiments of the device may include any of the features of any of the devices described herein, as well as any one of the following features.

The at least one housing may include an opening to provide access to the seal to enable actuation of the seal to control exposure of the at least one cell to air.

The seal may be secured to at least one surface of the source of energy through which air comes in contact with air-reactive parts of the source of energy.

The at least one housing may include a reusable part housing including a driving mechanism and a processor, and a disposable part housing including a reservoir to hold a therapeutic fluid and the source of energy, the source of energy provides energy to the driving mechanism and/or processor.

In yet another aspect, a method of manufacturing a therapeutic fluid infusion device is disclosed. The method includes providing at least one housing to retain a source of energy to energize the device, the source of energy including at least one electrochemical cell to produce electrical energy upon exposure of the at least one cell to air and a seal to prevent exposure of the at least one cell to air when the device is not in use and to enable exposure of the at least one cell to air prior to commencing operation of the device. The at least one housing includes an opening to provide access to the seal to enable actuation of the seal to control exposure of the at least one cell to air. The method also includes connecting the source of energy to the at least one housing such that the seal is accessible through the opening of the at least one housing.

Embodiments of the method may include any of the features of any of the devices described herein, as well as any one of the following features.

Connecting the source of energy may include integrally connecting the source of energy such that the source of energy cannot be removed.

Integrally connecting the source of energy may include affixing the source of energy to the at least one housing.

Affixing the source of energy to the at least one housing may include performing one or more of for example, soldering the source of energy to the at least one housing and/or encasing the source of energy in the at least one housing.

Providing at least one housing may include providing a dedicated energy source cover to retain at least the source of energy separate from at least another of the at least one housing of the infusion device. The method may further include connecting the dedicated energy source cover to the at least other of the at least one housing of the infusion device.

In another aspect, a portable fluid dispensing device for infusing a fluid into a body of a user and/or for sensing a bodily analyte is disclosed. The device includes a dispensing unit comprising a reservoir to hold a therapeutic fluid and a driving mechanism to dispense the therapeutic fluid to the body of the user, and a cradle unit to secure the dispensing unit to the body of the user. The cradle unit includes a source of energy to energize the dispensing unit, the source of energy comprising at least one electrochemical cell to produce electrical energy upon exposure of the cell to air.

Embodiments of the device may include any of the features of any of the devices and method described herein, as well as any one of the following features.

The cradle unit may include at least one air vent opening to enable air to be delivered to the source of energy.

The cradle unit may further include a semi-permeable membrane placed in the at least one air vent opening, the semi-permeable membrane configured to enable entry of air into the cradle unit and to substantially prevent entry of at least some other materials into the cradle unit.

The dispensing unit may include a reusable part including the driving mechanism and a disposable part having the reservoir. The dispensing unit may be operable upon connection of the reusable part and/or the disposable part to the cradle unit via establishment of electrical communication between the source of energy and the dispensing unit.

The dispensing device may further include a seal to prevent exposure of the at least one electrochemical cell to air when the source of energy is not in use and to enable exposure of the at least one cell to air prior to energizing the dispensing unit with the source of energy.

The cradle unit may be manufactured in a manner such that a portion of the cradle unit retaining the source of energy is integrally formed around the energy source such that the energy source cannot be removed.

The at least one electrochemical cell may include at least one Zinc-Air cell.

BRIEF DESCRIPTION OF THE DRAWINGS

FIGS. 7a-d are views illustrating implementations of a dispensing device and/or batteries with sealing.

DETAILED DESCRIPTION OF THE INVENTION

Disclosed is a portable fluid dispensing device and method for infusing a fluid into the body of a user and/or for sensing an analyte within the body. The device includes at least one housing to retain a source of energy to energize the device, the source of energy comprising at least one electrochemical cell to produce electrical energy upon exposure of the cell to air, and a seal to prevent exposure of the at least one cell to air when the source of energy is not in use and to enable exposure of the at least one cell to air prior to energizing the device with the said source of energy. The at least one housing includes an opening to provide access to the seal to enable actuation of the seal to control exposure of the at least one cell to air. In some embodiments, a portable fluid dispensing device is disclosed that includes a source of energy to energize the device, the source of energy comprising at least one electrochemical cell to produce electrical energy upon exposure of the cell to air, at least one housing to retain the source of energy, and a seal to prevent exposure of the at least one cell to air when the source of energy is not in use and to enable exposure of the at least one cell to air prior to energizing the device with the said source of energy. The at least one housing is manufactured in a manner such that a portion of the at least one housing retaining the source of energy is integrally formed around the energy source such that the energy source cannot be removed.

Figure 1A:
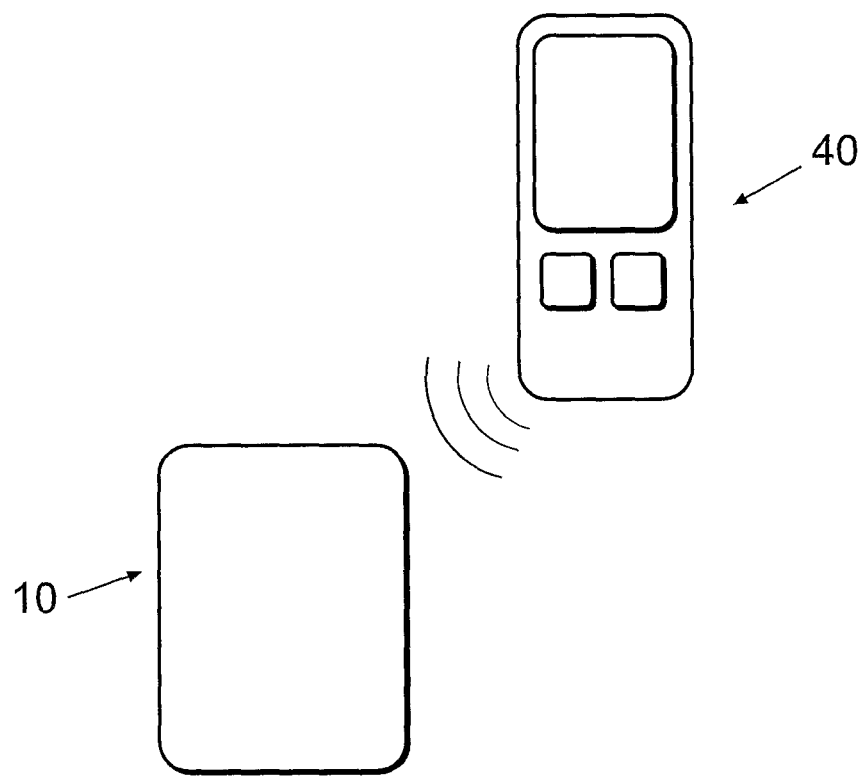
FIGS. 1a-c are schematic diagrams of exemplary single-part and two-part infusion pumps with and without a remote control unit.
Figure 1B:
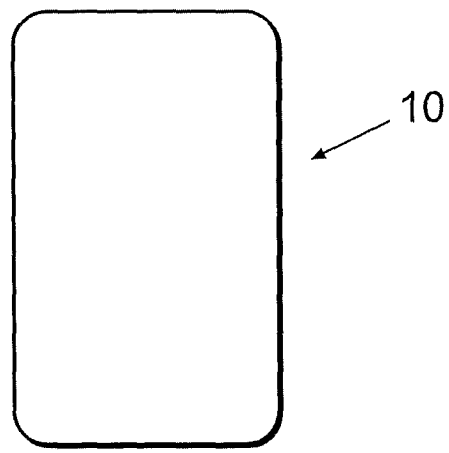
Figure 1C:
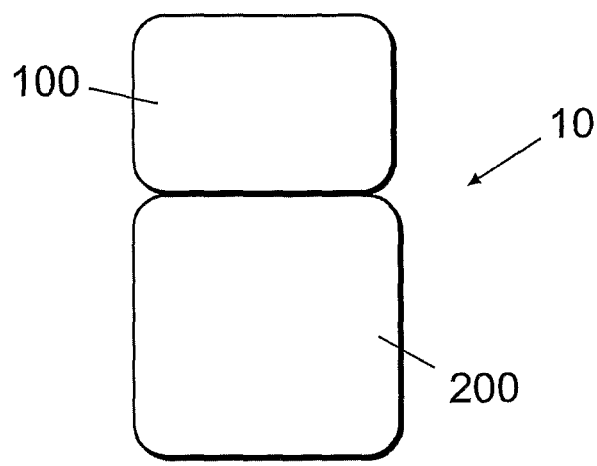

Referring to FIG. 1a, a schematic diagram of an exemplary fluid delivery device, also referred to as an infusion pump, is shown. The infusion pump of FIG. 1a comprises a dispensing patch unit 10 which is securable (e.g., adherable) to a patient's body, and a remote control unit 40, which communicates with the patch unit 10. The patch unit 10 may be composed of a single part (as shown, for example, in FIG. 1b) or of two parts (as shown, for example, in FIG. 1c) that include a reusable part 100 and a disposable part 200. The patch unit 10 (also referred to as a dispensing unit) may employ different dispensing mechanisms, such as a syringe-type reservoir with a propelling plunger, a peristaltic positive displacement pump, etc.

Figure 2A:
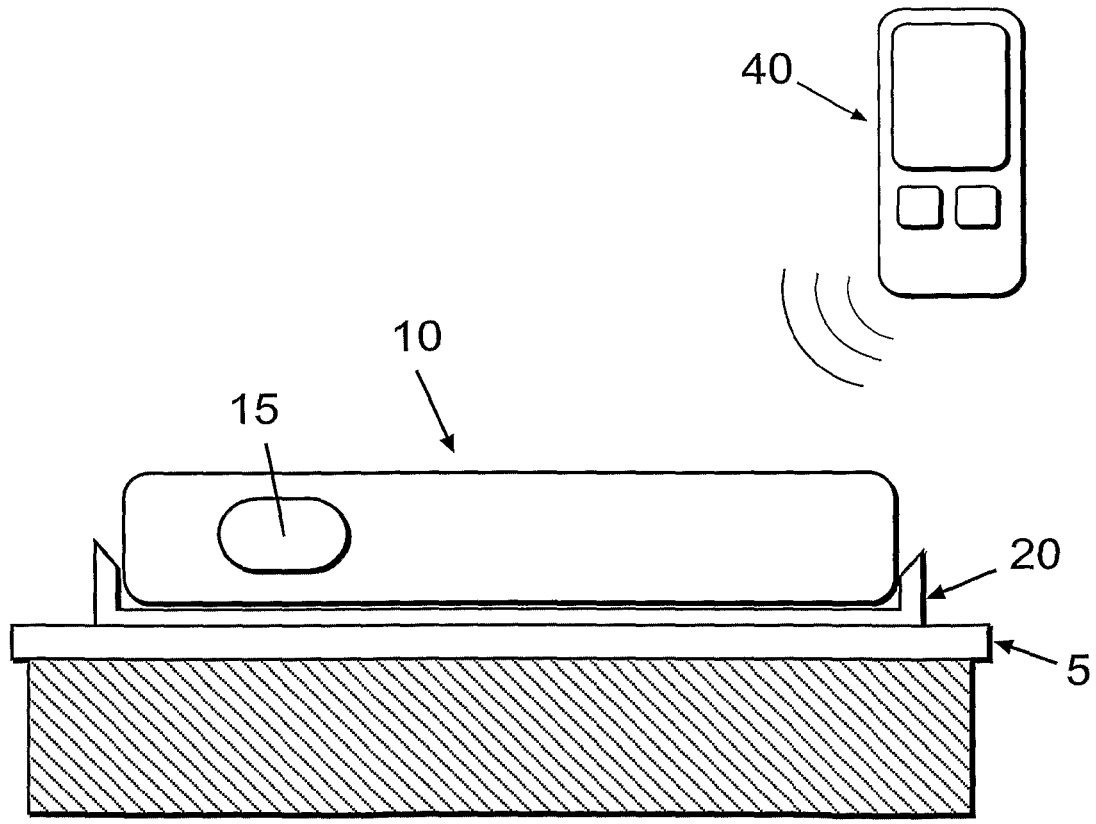
FIGS. 2a-b are schematic diagrams of exemplary single-part and two-part infusion pumps, respectively, that are attached to a patient's skin using a cradle.

Referring to FIG. 2a, a schematic diagram of an exemplary fluid delivery device comprising a single-part patch unit 10, a cradle unit 20 and a remote control unit 40 is shown. The patch unit 10 is connected to the cradle unit 20 after the cradle unit 20 is secured (e.g., through some adhesive mechanisms) to a patient's skin 5. The patch unit 10 may be disconnected from, or reconnected to, the cradle unit 20 at the patient's discretion. A needle unit that includes a cannula and a penetrating member (not shown) may be inserted through the cradle unit into the body of the patient. Fluid delivery can be programmed by a remote control unit 40 or programmed or controlled manually through at least one button 15 provided on the patch unit 10.

Figure 2B:
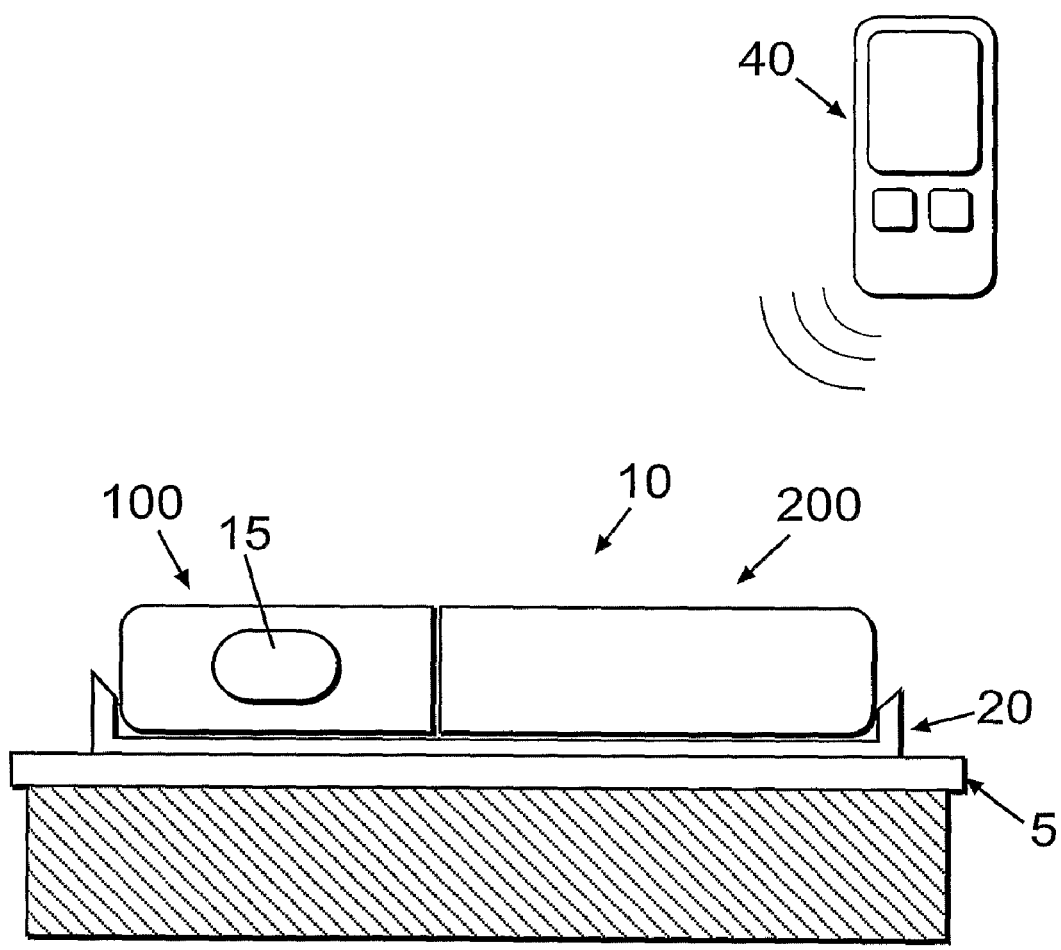

Referring to FIG. 2b, a schematic diagram of an exemplary fluid delivery device comprising a two-part dispensing unit 10 with a reusable part 100 and a disposable part 200, a cradle unit 20 and a remote control unit 40 is shown. One or more manual buttons 15 may be located on the housing of the reusable part 100 of the patch unit 10.

The configurations of the fluid delivery device comprising a patch unit, a cradle unit and a needle unit as detailed herein are described, for example, in co-owned Israeli Patent Application No. IL 171813, U.S. Publication No. 2007/0106218, U.S. application Ser. No. 11/706,606 and U.S. Provisional Patent Application Nos. 60/833,110, 60/842,869 and 60/848, 511, the contents of all which are hereby incorporated by reference in their entireties. One of the advantages of these configurations is that the relatively expensive components of a fluid delivery device may be deployed within the reusable part of the device while the relatively less expensive components, including, for example, a power source, may be accommodated within the disposable part. A dispensing unit (i.e., patch unit) conforming to such configurations and arrangements (i.e., arrangement having a reusable and disposable parts) may render use of a therapeutic fluid dispensing device more economical for the manufacturer, for the device provider and/or for the patient. These arrangements, particularly arrangements in which an inexpensive power source (e.g., battery) is housed within the disposable part of such a dispensing device, may also avoid the inconvenience of replacing batteries as they would be replaced together with the disposable part. Such device arrangements also make it unnecessary to carry replacement batteries in addition to the infusion pump. Furthermore, replacement procedures to replace the power source (e.g., the batteries) are simplified in that replacement of the power source is reduced to replacing the entire disposable part, with the batteries contained therein, of the dispensing device (as shown, for example, in FIGS. 3 to 5) thus avoiding the need to utilize specialized tools, parts or skills to replace the actual power source. However, in some embodiments, replacement of a battery may be performed separately and/or independently from the replacement of the disposable part.

Figure 3:
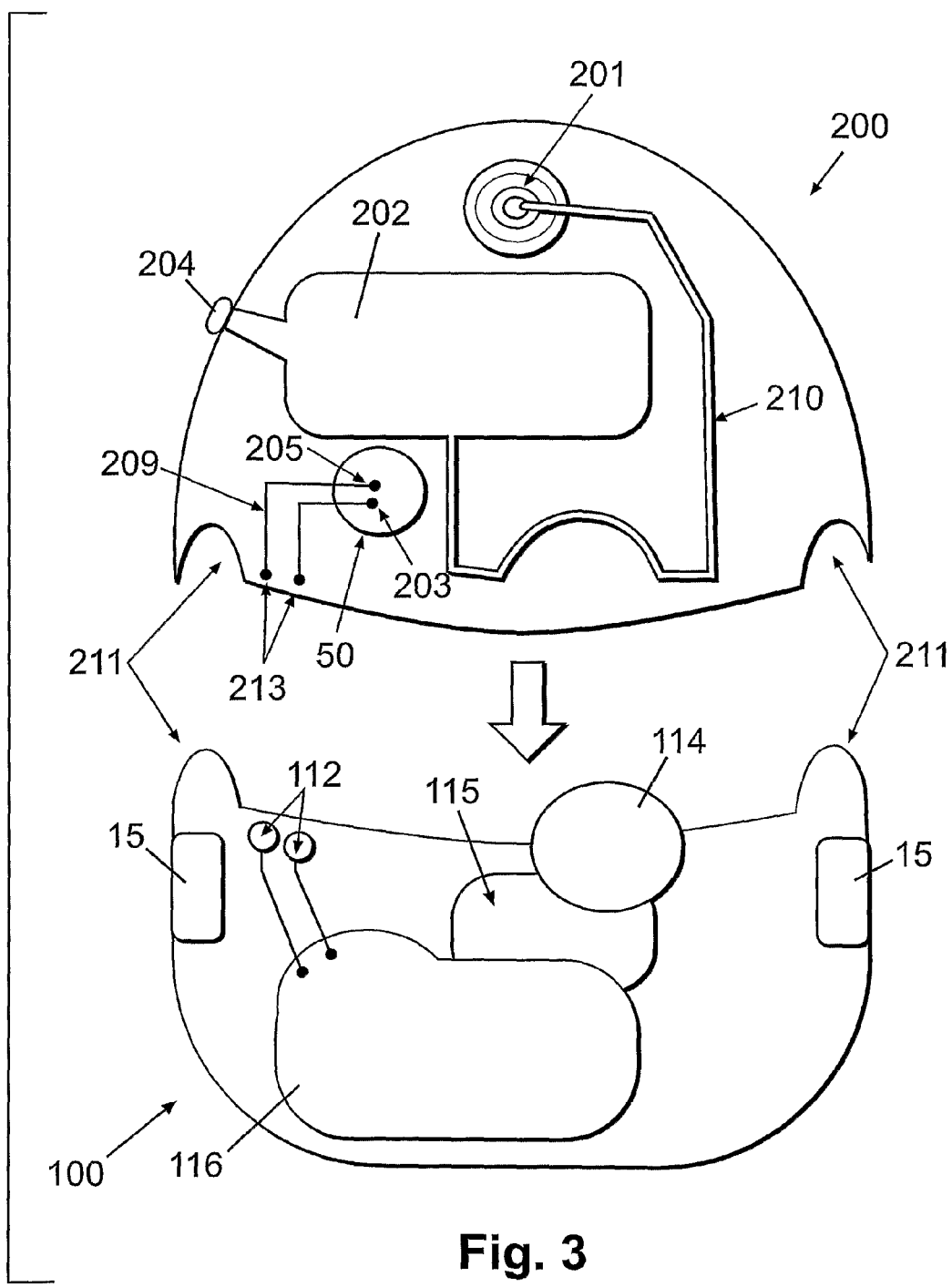
FIG. 3 is a schematic diagram of an exemplary peristaltic infusion pump with a reusable part and a disposable part.

Referring to FIG. 3, a schematic diagram of an exemplary peristaltic infusion pump with a disposable part 200 and a reusable part 100 is shown. The disposable part 200 and the reusable part 100 are depicted in FIG. 3 in a pre-attachment configuration (i.e., prior to attachment of the parts to each other). The disposable part comprises:
An outlet port 201 to deliver therapeutic fluid to the patient's body.
A reservoir 202 for storing the therapeutic fluid.
An inlet port 204 to fill the reservoir 202 with the therapeutic fluid.
A delivery tube 210 to connect the reservoir 202 to the outlet port 201.

A battery 50 to serve as a power source to power the electrical components of the infusion pump. In some embodiments, the battery is electrically coupled through the cathode connectors 203 (only one such cathode connection is shown) and an anode connector 205. These connectors are wired to the electrical components in the reusable part via, for example, standard quick connectors such as Ultra-Fast Receptacles & Tabs (FASTON™) commercially available from Tyco Electronics Corporation, or simply by metal tabs aligned to each other. In some embodiments in which metal tabs are used, the metal tabs are soldered to a PCB 116 at one side and/or to the battery 50 at the other side. For example, the FASTON™ tabs 213 can be provided in the disposable part and the FASTON™ housings 112 may be placed in the reusable part 100. Other techniques and mechanisms can be used to provide electrical connection between the battery and other electronics of the dispensing unit.
A set of wires 209 that connect the battery from the cathode connectors and the anode connector to the standard quick connectors in the disposable part, and from the standard quick connectors in the reusable part to the electrical circuit.
The reusable part 100 may comprise:
One or more manual buttons 15 to adjust the amount of therapeutic fluid needed to be delivered, e.g., a bolus dosage to be delivered.
A driving mechanism 115 including a motor and a gear (the motor and gear are not shown in the figure).
A rotary wheel 114 that, combined with the driving mechanism and/or with at least a portion of the delivery tube, constitute a peristaltic pump
A PCB 116 with electronic components.

Each part (e.g., the disposable part and the reusable part) may also have a coupling mechanism 211 to pair to the other part. Such a mechanism may include a magnet or any other known mechanical connector device such as clips, a clamp, a rail, a cog, etc. The electrical connectors can be combined with the coupling mechanism such that when mechanically attaching the two parts (e.g., the disposable part and the reusable part) together, the electrical components concomitantly electrically couple to the battery (e.g., via the various electrical connectors). Such connections are also available from Tyco Electronics Corporation.

Figure 4:
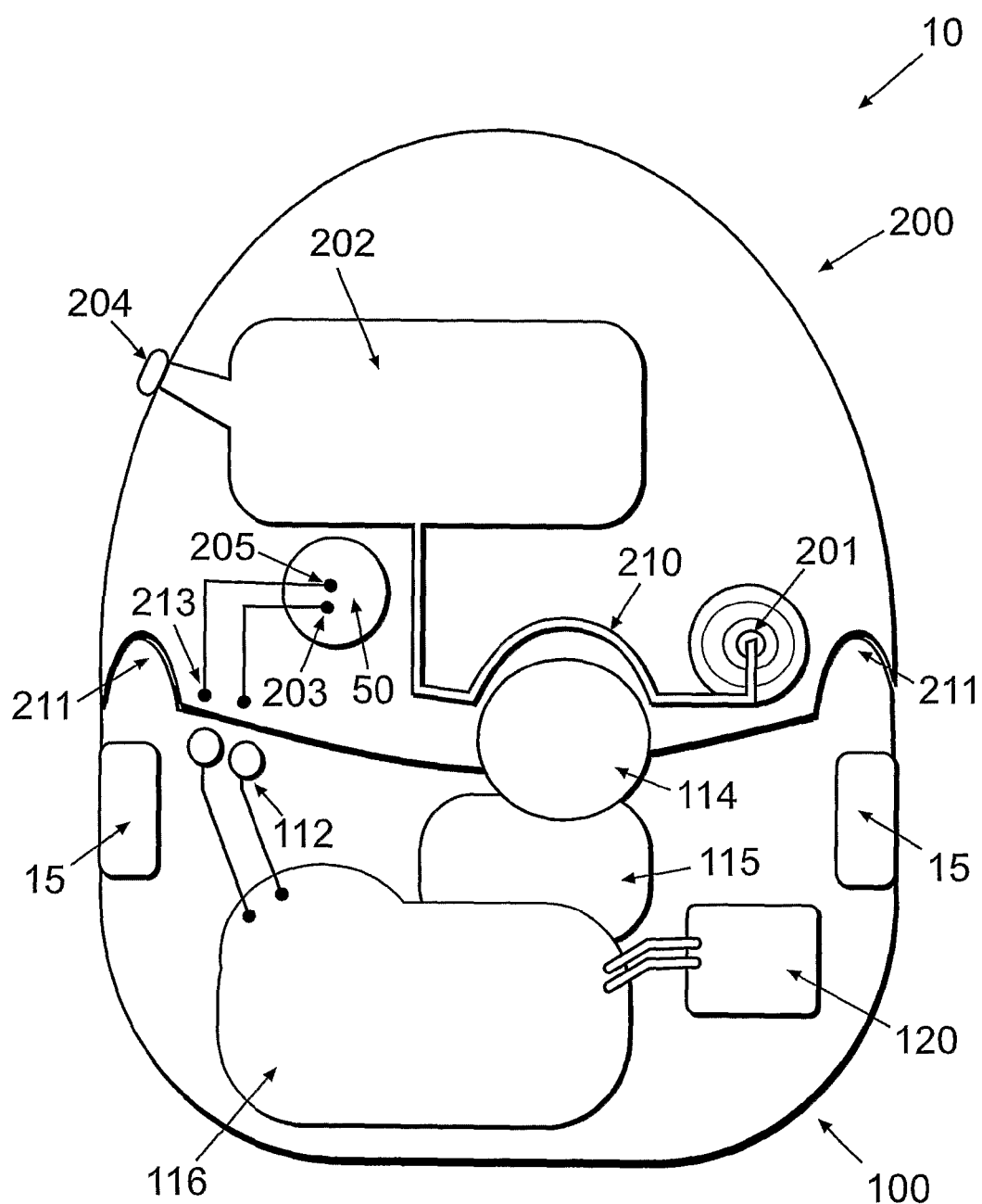
FIG. 4 is a schematic diagram of an exemplary peristaltic infusion pump with a sensor.

Referring to FIG. 4, a schematic diagram of an exemplary peristaltic infusion pump 10 with disposable part 200 and the reusable part 100 attached to each other is shown. The infusion pump 10 also includes a sensor 120 to monitor a body analyte (e.g., glucose). Fluid delivery can be adjusted based on the monitored body analyte to thus implement a semi, or fully, closed-loop system.

Figure 5:
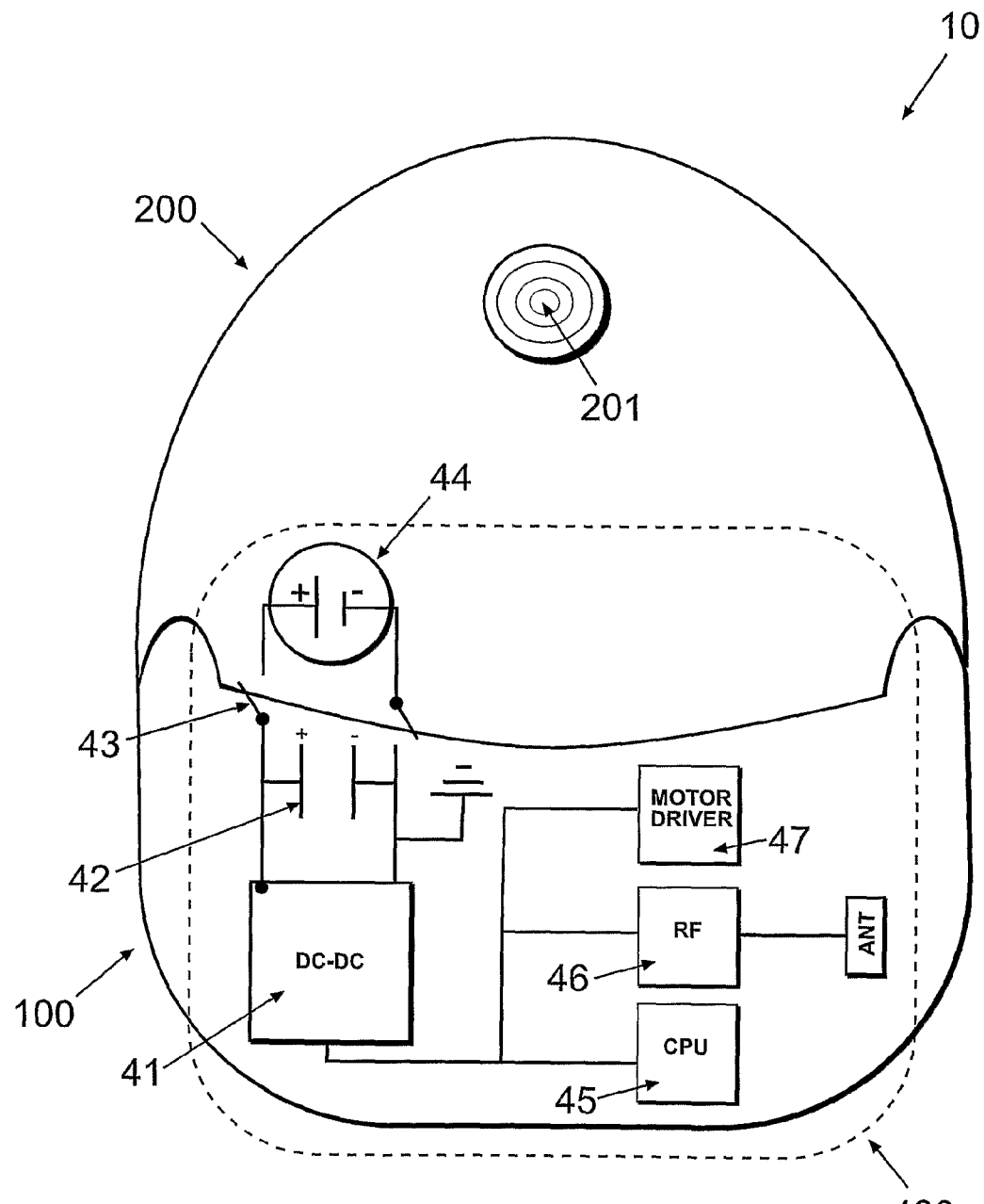
FIG. 5 is a schematic diagram of an exemplary two-part infusion pump with a block diagram of an exemplary electrical arrangement used for the pump.

Referring to FIG. 5, a schematic diagram of an exemplary two-part infusion pump, including a block diagram depicting the electrical arrangement housed in the reusable part, is shown. When the two parts are attached to each other, an electrical circuit 400 is closed by electrically connecting the power source 44, to the other components of the electrical circuit. The power source may include one or more button batteries such as, for example, zinc/air batteries.

The electrical circuit includes a motor driver 47 and a CPU 45 to control and monitor the activity of the pump. The CPU 45 may be placed on a Printed-Circuit Board (PCB), as shown, for example, in FIGS. 3 and 4 as the element marked as reference numeral 116. Also connected to the electrical circuit are a receiver 46 and a DC-DC step up converter 41. Thus, the connectors that include housings and tabs (respectively marked, in FIGS. 3 and 4, as reference numeral 112 and 213) that may implement the functionality of the switches 43 (shown in FIG. 5) which switch on the electrical components of the infusion pump upon mechanical connection of the disposable and the reusable parts. Also shown in FIG. 5 is the outlet port 201 to deliver the therapeutic fluid.

As further shown in FIG. 5, is the electrical arrangement of the circuit 400 implemented in the reusable part includes a capacitor 42, such as a high capacity capacitor of more than 100 mF capacity. In some embodiments, the capacitor has a capacity of at least 180 mF capacitor. The capacitor is configured to accumulate sufficient charge so that a higher current than what can be generated by the battery by itself may be provided to power components requiring that higher current level. The capacitor is charged by the battery for a particular period of time and then releases the charge over a relatively short period of time. The relation between the time during which the capacitor is charged with current supplied by the power source (e.g., the battery) and the time during which the capacitor is discharged may be controlled, for example, by the CPU 45 and/or by a suitable electrical circuit arrangement to control the charge and discharge periods (e.g., selecting resistance and capacitance values introduced into the arrangement to affect the charge and discharge periods of the capacitor). In some embodiments, the time duration during which the capacitor is loaded may be 490 milliseconds, and the time duration during which the capacitor is discharged may be 20 milliseconds. Under these circumstances, if the battery's output current is 10 mA, the capacitor discharge output is about 500 mA, the discharge time would therefore be approximately 50 shorter than the charging time to charge the capacitor. Accordingly, employing a high capacity capacitor or some energy storage device enables to effectively increase the power output of low-energy output batteries such as zinc/air batteries for short period of time, also known as pulsed power. In some embodiments, the time interval for charging the capacitor may be at least twenty (20) times longer than the time interval to discharge the capacitor. The time interval to charge the capacitor may overlap, at least in part, the time interval to discharge the capacitor.

In some embodiments, instead of using standard size (AA or AAA) lithium or alkaline batteries, fuel cells (e.g., zinc air batteries) are used as an energy source. Use of zinc/air batteries enables manufacturing of relatively small dimensioned patch units. Particularly, whereas the smallest dimension of standard AAA battery is 10.5 mm (the battery's diameter), the smallest dimension of standard zinc/air battery (e.g., DA10 or DA312 made by DURACELL™) is, for example, 3.5 mm. The larger battery dimensions of standard AA and/or AAA batteries result in heavier and larger infusion patches and/or insulin pumps (because larger housings would be required to accommodate such batteries), and also increase the costs of these devices. Typical insulin pump devices weigh about 85 g and have a height of about 15 mm. In contrast, some embodiments of infusion pumps in described herein weigh about 20g and are less than 15 min in height and in some embodiments the smallest dimension is less than 15 mm.

Zinc-air batteries, also called "zinc-air fuel cells", are non-rechargeable, electrochemical batteries powered by the oxidation of zinc with oxygen from the air. These batteries have very high energy densities and are relatively inexpensive to produce. They are mainly used in hearing aids as described, for example, in U.S. Pat. Nos. 5,591,541, 5,607,796, 5,662, 717, 5,733,676 and 5,804,327, the contents of all of which are hereby incorporated by reference in their entireties. Zinc-air cells generally work like conventional batteries, i.e., the batteries generate electrical power from chemical reactions. However, instead of packing the necessary materials (ingredients) inside the cell, zinc-air batteries get one of their main reactants, namely, oxygen, from the outside air. Using a reactant from the air reduces the size and space requirements of the battery, and thus reduces the dimensions and weight of the device retaining the battery. Also, unlike some batteries used in wireless devices, zinc-air cells contain no toxic compounds and are neither overly reactive nor flammable. Thus, zinc-air batteries can be recycled and safely disposed of. Other advantages of zinc air batteries includes:

High specific energy compared to other batteries (110-200 Wh/kg or 400-720 kJ/kg).
Providing continuous energy as the battery is depleted of its energy; the battery's voltage does not drop until the battery is depleted by over 80-85%.
Very long shelf lives as long as the zinc-air batteries are properly sealed to prevent oxygen from reacting with the batteries' cells until the batteries are activated for use.
Low Operating Cost—Zinc-air cells and batteries offer a low operating cost on a per-milliampere-hour basis when used in frequent or continuous use applications.
Typically, these batteries are button-type Zinc-air batteries, which are smaller and lighter than the common alkaline or lithium batteries that are currently in use.

On the other hand, zinc/air batteries:
1. require a continuous supply of oxygen; and
2. sometimes may not have sufficient power (e.g., current of about 10 mA and voltage of approximately 1.2 volts) to operate some of the energy-consuming components of infusion devices, such as devices motor and processor used with infusion devices. Under those circumstances, an electrical arrangement that includes one or more capacitors to provide sufficient charge to power, at least initially, the high energy demand of such components of the dispensing device may be used, as described herein.

Figure 6A:
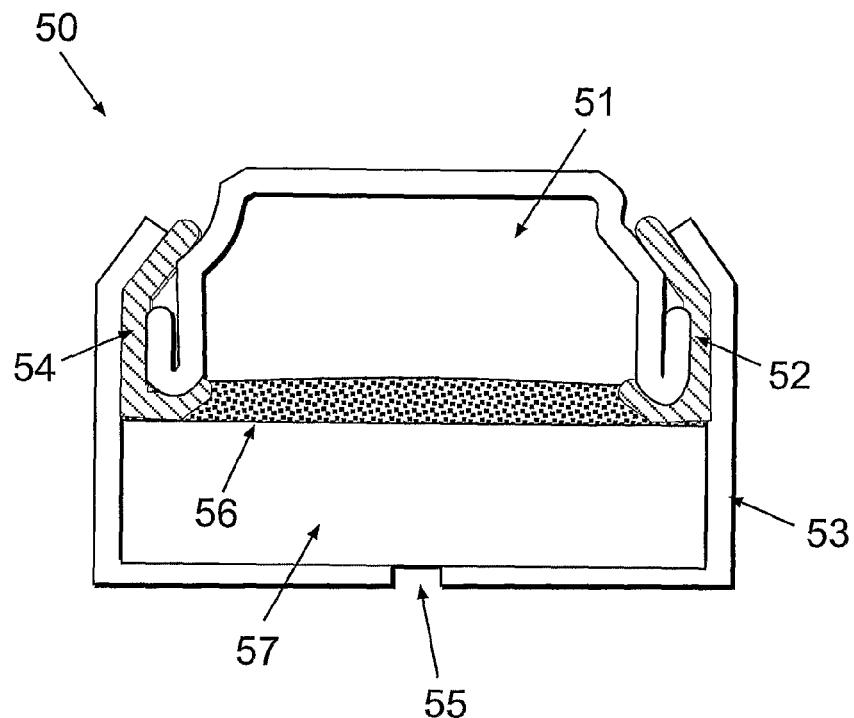
FIGS. 6a-b are cross sectional schematic diagrams of exemplary zinc/air batteries.
Figure 6B:
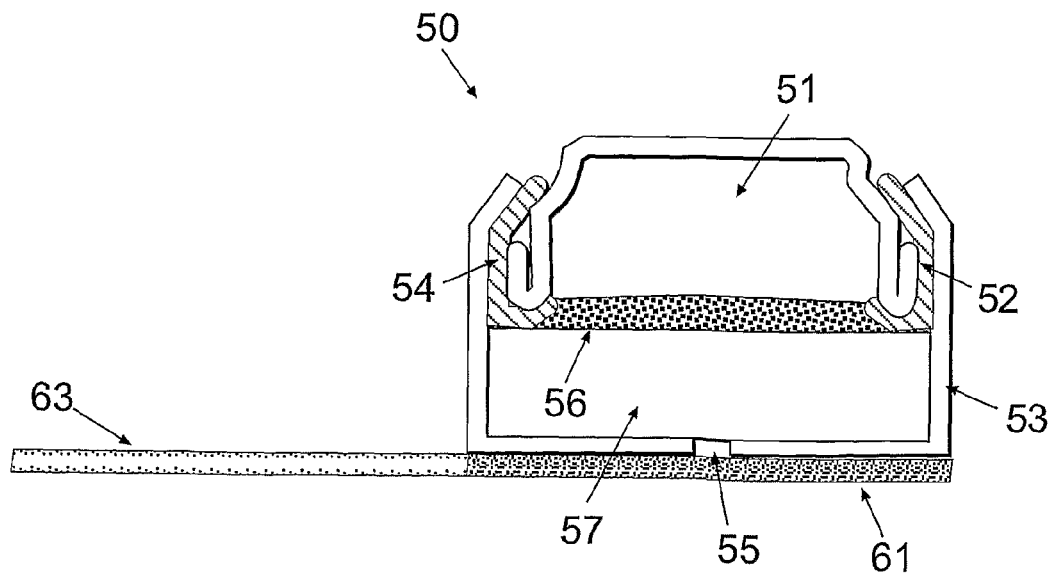

Referring to FIGS. 6a and 6b, cross-sectional schematic diagrams of an exemplary zinc/air battery 50 are shown. FIG. 6a shows the battery in active mode, without a seal, thus enabling the chemical reaction that consumes $O_{2(g)}$, found in the ambient air, to occur. FIG. 6b shows the battery 50 as it is provided by the manufacturer with its cathode chamber sealed with a sealing mechanism 61 (e.g., a peelable seal).

The battery 50 includes a cell having a zinc anode chamber 51 in which zinc is oxidized upon the introduction of air, which includes oxygen, into the air cathode chamber 57 in which reduction of oxygen to water takes place, thus creating an electrical potential difference. Oxygen can enter the air cathode chamber through at least one air access opening 55 provided in a wall of the air cathode chamber. The opening is required because the reduction reaction requires a constant supply of oxygen. Generally, and as shown in FIG. 6b, the battery is provided by the manufacturer with its air cathode sealed, thus preventing the activation of the battery while it being shipped and stored. The seal 61 (or some other type of sealing mechanism) that controls the entry of oxygen into the cathode chamber of the cell may be actuated to cause air to enter the cell. For example, in circumstances in which the seal 61 includes a removable tab that covering the opening 55, the seal is removed by pulling its tab 63 before the battery can be used to supply energy.

As further shown, in some embodiments, the two chambers are separated by a barrier 56 and each of the chambers is enclosed in a separate housing (i.e., a shell or a can): an anode can 54 and a cathode can 53. The cans are isolated from each other by a gasket 52 to prevent discharge Referring to FIGS. 7a to 7d, views depicting operation of exemplary sealing mechanisms that control air entry into energy sources (e.g., batteries) are shown. Particularly, the figures show the removal of a battery's seal 61 by pulling the seal's tab 63. The seal isolates the cathode can from ingress of oxygen, thus preventing the unnecessary (i.e., premature) oxidation of the zinc in the battery prior to commencing use of the battery to power, for example, a dispensing device. Therefore, the battery 50 remains inactive as long as it is sealed. While the battery is inactive, its shelf life is significantly prolonged, thus also extending the shelf life of the disposable part.

FIG. 7a shows a sealing mechanism that includes a peelable seal (for example, a circular cover that covers substantially the entire surface area of the cathode or of the opening through which air would enter the battery) attached to a pull tab. The battery's seal is attached directly to the battery, and may be placed onto the battery by the manufacturer of the battery. This configuration requires only that the battery be connected to the infusion pump with no further processing. In such embodiments, the battery may be placed in the infusion pump during the manufacturing (e.g., assembly) process to produce the pump such that the infusion pump already includes the sealed battery in condition for immediate use upon removal of the seal. In some embodiments, the power (energy) source is integrally connected to the infusion pump (e.g., to the disposable part of a two-part infusion pumps) such that it cannot easily, or at all, be removed or replaced. For example, the sealed power source may be connected to the infusion pump by soldering.

By using the battery with the original seal (e.g., provided by the battery manufacturer), an opening for the seal's tab (numeral 65 in FIG. 12b) may be left in the housing (cover 66) of the disposable part. The opening would thus provide access to the sealing mechanism of the energy source that controls the entry of air to the battery, and would enable actuation of the sealing mechanism, prior to commencing operation of the patch unit, to enable entry of air to the battery. In circumstances in which a seal with a tab 63 is used to implement the sealing mechanism, the tab 63 is placed outside the cover while the battery 50 is placed within the disposable part in a dedicated cover 64 (also referred as battery's housing). The opening would enable the removal of the seal 61 by pulling the tab. Upon removal of the seal, ingress of oxygen into the battery is enabled and the battery is activated (as shown, for example, in FIGS. 7c and 7d).

As further shown in FIGS. 7a-d, a selective membrane 62 may be placed in an opening to enable ingress of oxygen to the battery. Further details regarding the use of such a selective membrane is provided, for example, in the commonly-owned provisional application No. 60/961,382, entitled "Vented Dispensing Device and Method" and the non-provisional application entitled "Vented Dispensing Device and Method", being filed on the same day as the current application, the contents of both of which are hereby incorporated by reference in their entireties. The selective membrane (also referred to as breathable membrane) has a selective permeability. It protects the battery from harmful materials such as water and other liquids, but enables oxygen ingress. The membrane may be made from waterproof materials and/or waterproof fabrics such as, for example, waterproof/breathable fabrics that provide gas diffusion through the membrane but repel water. An example of such a suitable fabric is GORE-TEXT™, described, for example, in U.S. Pat. No. 4,194,041, the content of which is hereby incorporated by reference in its entirety.

In some embodiments, the membrane is covered with a seal that is removed just before use of the battery begins. The seal is made of impermeable material, which prevents oxygen ingress and thus gives the battery prolonged shelf life.

Referring to FIG. 7b, a view of another exemplary embodiment of an infusion pump with a sealing mechanism is depicted. As shown, a seal is placed on the external side of the selective membrane (e.g., at the exterior of the infusion pump). In this embodiment the cover should be air tight to prevent energy depletion of the battery. In some embodiments, the infusion pump can be packaged in a substantially air tight enclosure to enable the sealing of the battery.

Figure 7C:
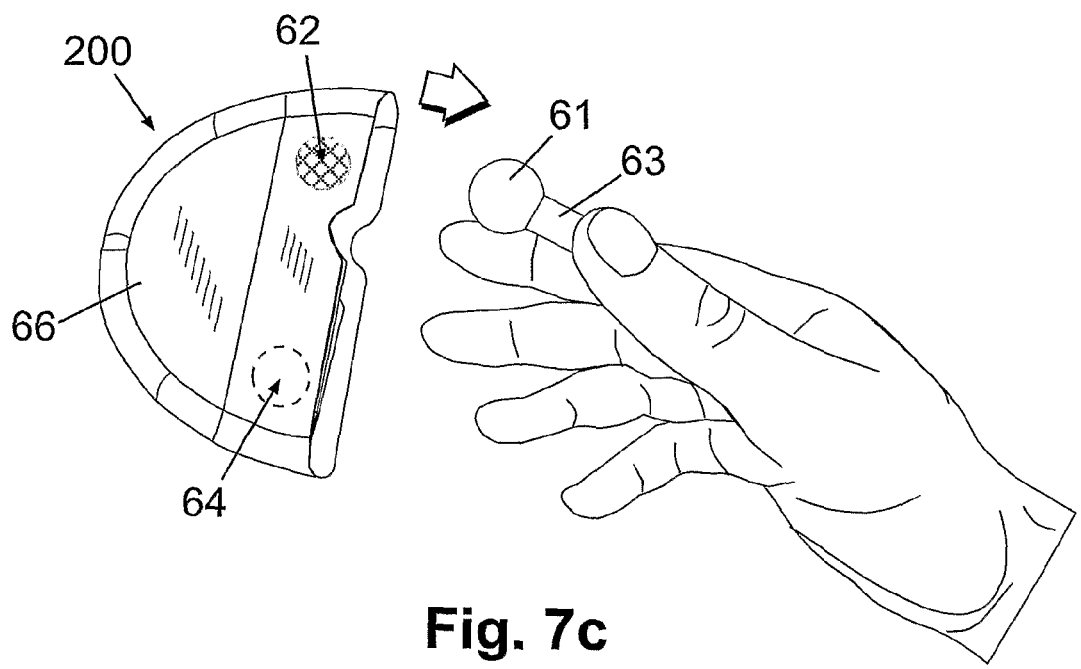
Figure 7D:
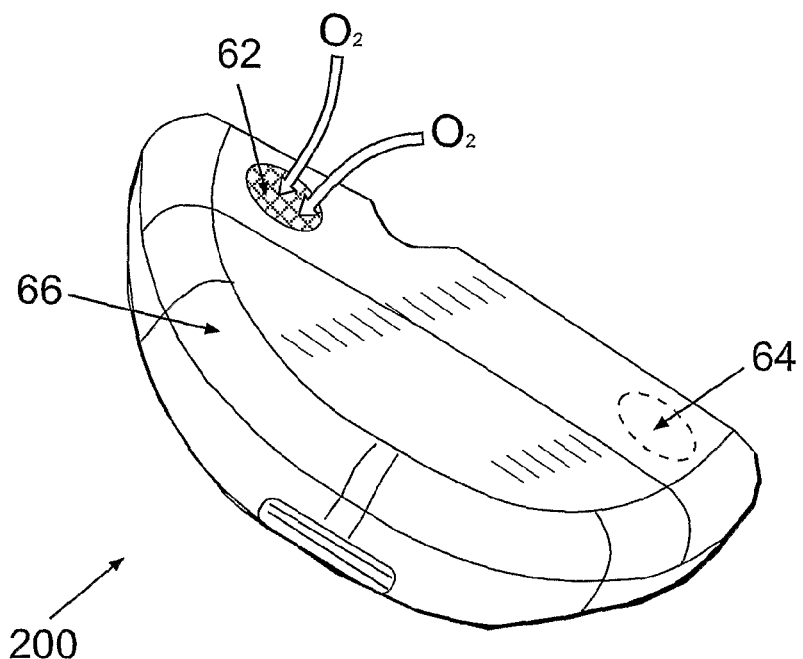

FIGS. 7c and 7d show the disposable part of the device after the removal of the seal. The seal's tab has been pulled by the user and thus oxygen is free to move from the exterior of the infusion pump to the battery 50 through the membrane 62 (as shown in FIG. 7d).

Figure 8:
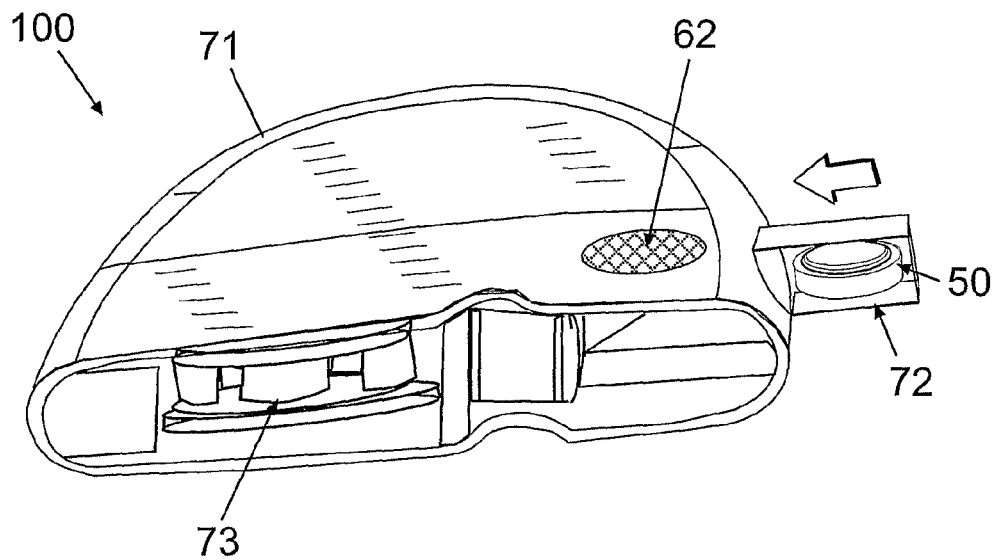
FIG. 8 is a view of illustrating an exemplary embodiment of the insertion of a battery to a reusable part of an infusion pump.

Referring to FIG. 8, a view illustrating an exemplary battery insertion approach is shown. In the illustrated approach of FIG. 8 the batteries are provided separately, i.e., not as an integral component of the cradle (as shown, for example, in FIG. 11) or in the disposable part of the device (as shown, for example, in FIGS. 3 to 5 and 7a to 7d). Therefore, in the illustrated embodiment of FIG. 8, the batteries are inserted into the pump and electrically connected thereto manually. FIG. 8 shows a single battery 50 without a seal or other type of sealing mechanism, being positioned in a dedicated pocket 72 (or housing) that is attachable to the external cover of the reusable part. The pocket can be detached from the cover 71 of the reusable part 100, when replacing the battery. Clearly, there can be more than one battery which may be inserted into the infusion pump. Also shown in FIG. 8 is the wheel 73 of the peristaltic mechanism (shown also in FIGS. 3 and 4 where it is indicated by reference numeral 114).

Figure 9:
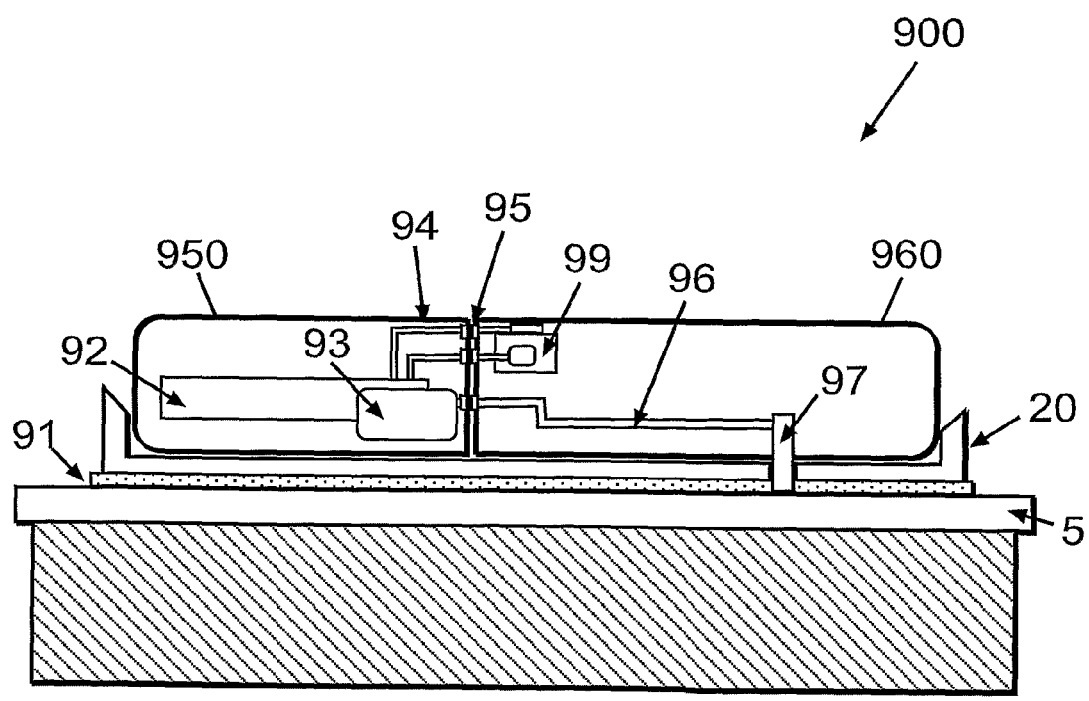
FIG. 9 is a cross-section schematic diagram of an exemplary two-part infusion pump attached to a patient's skin using a cradle.

Referring to FIG. 9, a cross-sectional diagram of a two-part system 900 is shown. The infusion pump 900 is implemented as a semi-closed loop and/or closed-loop system to sense analytes level (e.g., senses glucose) and dispense therapeutic fluid (e.g., insulin). The system includes one or more energy sources (e.g., button batteries) that are used to supply the energy needs of the closed loop system Details of exemplary closed-loop systems are described, for example, in co-owned U.S. patent application Ser. No. 11/706,606, the content of which is hereby incorporated by reference in its entirety. The system 900 includes two parts: a reusable part 950 containing the relatively more expensive components of the system, such as the CPU and other electrical components 92, a motor and, a driving mechanism (as shown, for example, in FIG. 4). The power for the electrical components, including one or more sensors 93, is supplied by one or more button batteries 99, such as zinc/air button batteries. The batteries may be placed in the disposable part 960 and are electrically connected to the electrical components by a set of wires 94. Plugs 95 are used to connect the reusable part to the disposable part. The plugs connect the main electric components of the system to the power source and also connect the probes 97 to the one or more sensors 93. The sensor 93 receives signals related to the bodily analyte (e.g., glucose) concentrations from one or more probes 97 and processes the signals to provide data regarding the bodily analyte concentrations. In some embodiments the sensor 93 may in integrate with the CPU and/or other electrical components 92. The sensor can be connected to the plugs by any standard mechanism, including wires and/or optical fiber 96. In some embodiments, the one or more probes 97 are coupled to a cannula which provides a passage to the user's body (as shown, for example, in FIG. 11).

In some embodiments, the system for sensing analyte and dispensing therapeutic fluid is attached to the user's skin by a cradle 20. The cradle may be attached to the user's skin 5 by adhesive 91.

In some embodiments, the energy requirements of a combined sensing and dispensing device, as described above, are met by button batteries. Moreover, the energy requirements of a device with only sensing capacity are also met by button batteries. Such a device for monitoring blood analytes is disclosed, for example, in co-owned U.S. provisional patent application Ser. No. 60/653,504, the content of which is hereby incorporated by reference in its entirety.

Figure 10:
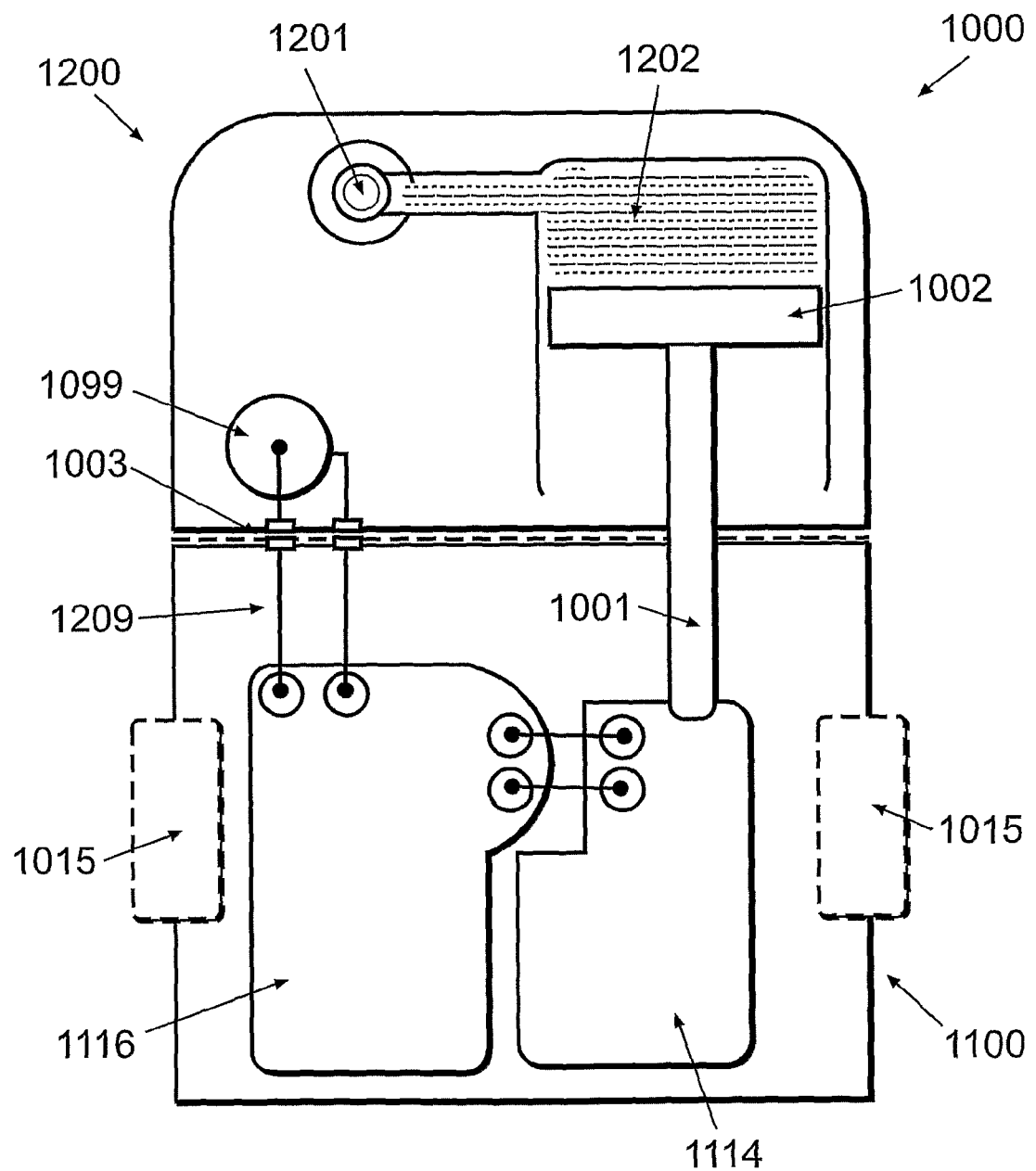
FIG. 10 is a schematic diagram of an exemplary two-part infusion pump employing a piston.

Referring to FIG. 10, a schematic diagram of an exemplary embodiment of a two-part infusion pump 1000 is shown. The infusion pump 1000 delivers therapeutic fluid by a propelling plunger mechanism, similar to the mechanism disclosed, for example, in PCT patent application No. PCT/IL08/000641, entitled "A positive displacement pump", filed May 11, 2008, the content of which is hereby incorporated by reference in its entirety. In some embodiments, the infusion pump 1000 comprises two parts: a reusable part 1100 and a disposable part 1200.

In some embodiments, the infusion pump includes:

An outlet port 1201 to deliver the therapeutic fluid to the patient's body.

A reservoir 1202 to store therapeutic fluid.

A power source 1099 that includes one or more batteries, to energize the electrical components of the infusion pump.

Wirings 1209 that electrically connect the battery and other electronic components to each other.

A user input interface that may include, in some embodiments, at least one manual button 1015 to adjust the amount of therapeutic fluid to be delivered, particularly for a bolus dosage.

A displacement driving mechanism 1114, including a motor and a gear. The driving mechanism moves a piston, which, in some embodiments, comprises a threaded rod 1001 and a plunger 1002.

Electronic components 1116, such as controller, processor and transceiver.

As a result of placing the power source in the disposable part 1200 and the more expensive electrical components in the reusable part, electrical connection between the two parts needs to be used. Such a connection 1003 can be implemented by simple metal (or other conducting material) plates that are pressed together when the two parts of the infusion pump are assembled together. Further details about electrically connecting the reusable and disposable parts are also provided, for example, with respect to FIGS. 3 and 4.

Figure 11:
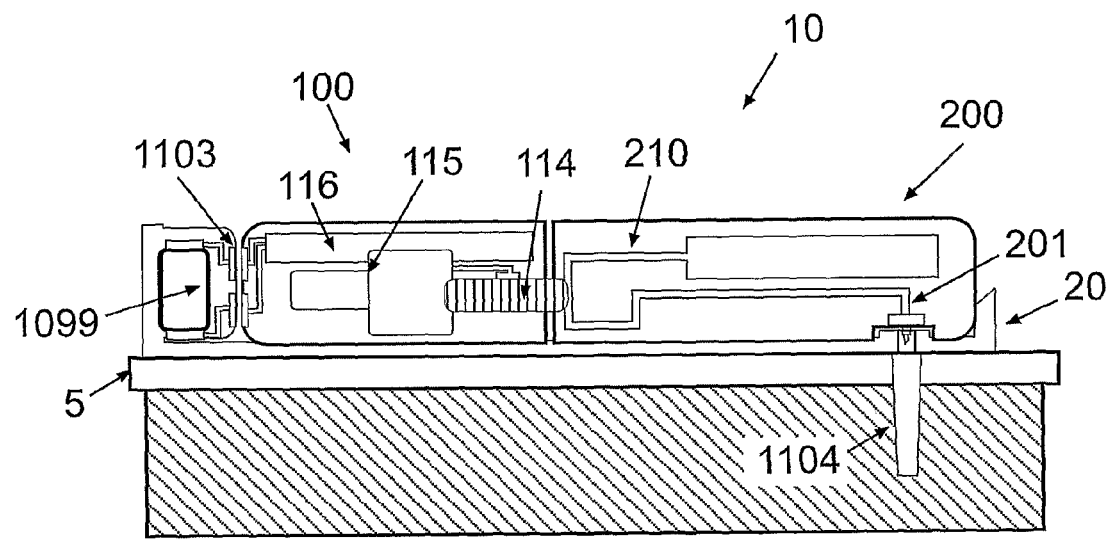
FIG. 11 is a schematic diagram of an exemplary peristaltic-type infusion pump with reusable and disposable parts attached to a patient's skin.

Referring to FIG. 11, a schematic diagram of a peristaltic-type two-part infusion pump is shown. At least one button battery is used as a power source 1099 for the infusion pump 10. In some embodiments, some or all of the batteries are placed in a cradle 20 that is secured to the user's skin 5. The power source is electrically connected to the electrical components 116 and to the motor and driving mechanism 115 of the reusable part 100 using a plug and socket connections 1103. FIG. 11 also shows a cannula 1104 that is used for delivering a therapeutic fluid to the user's body.

Figure 12A:
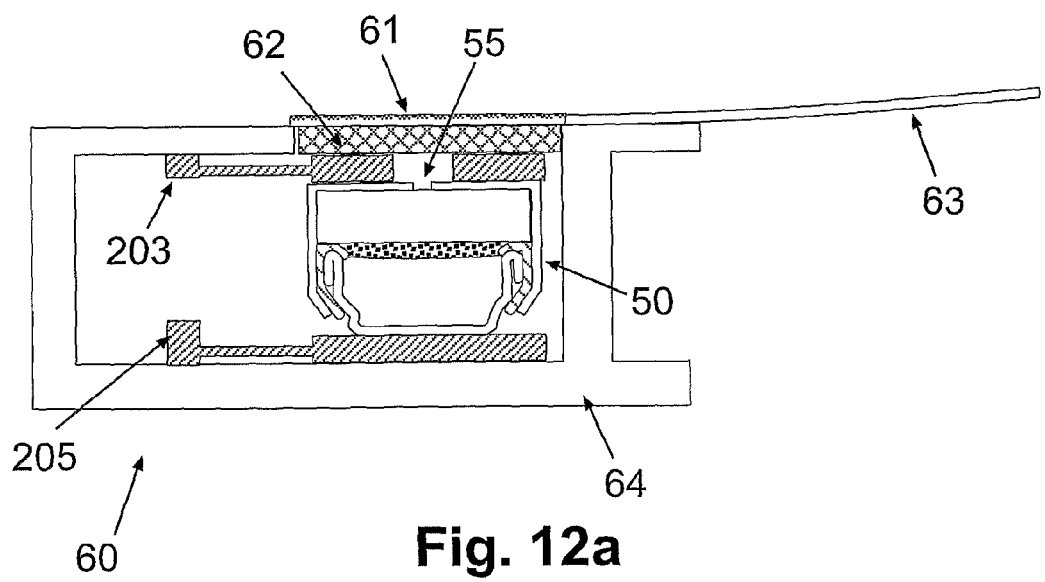
FIGS. 12a-e are diagrams of exemplary configurations for connecting a battery to an infusion pump.
Figure 12B:
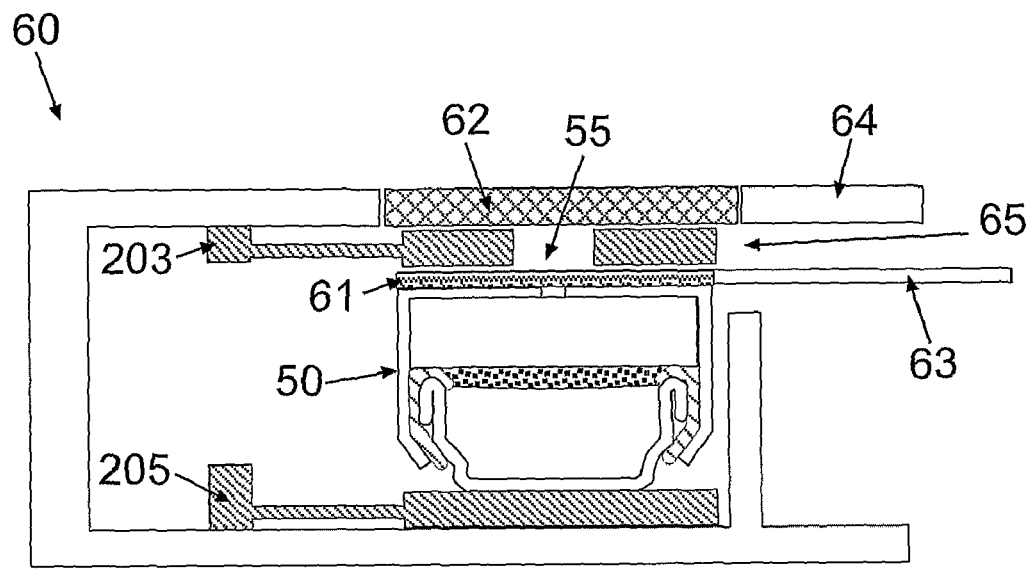
Figure 12C:
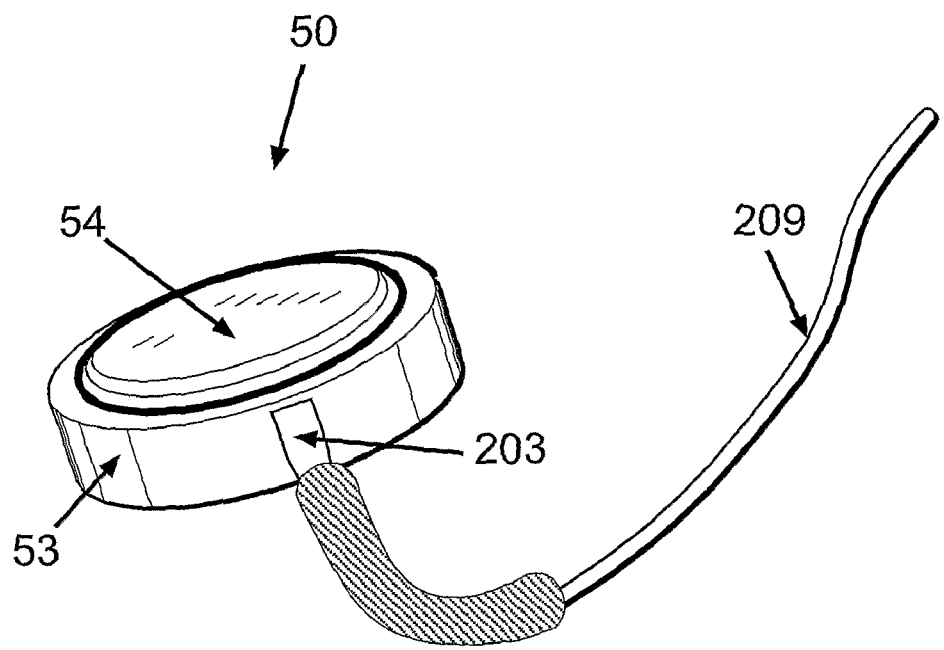
Figure 12D:
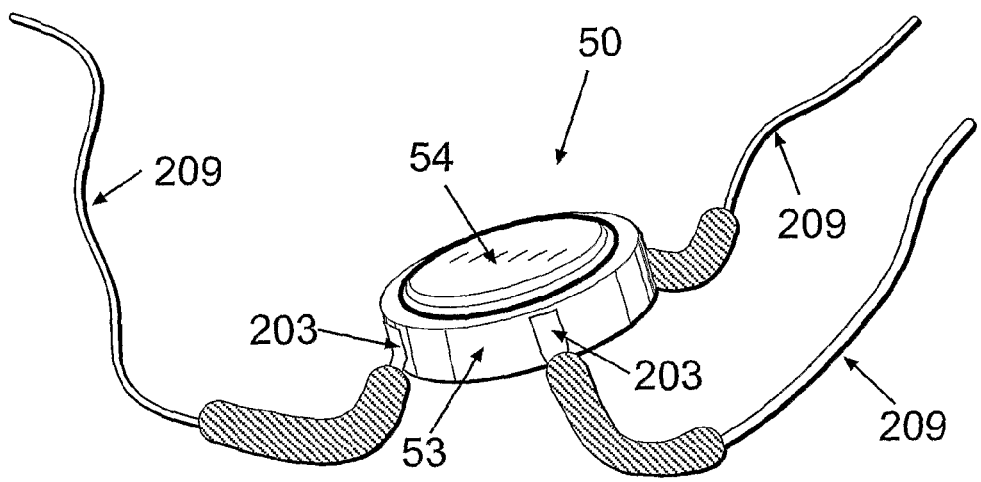

Referring to FIGS. 12a to 12d, schematic diagrams of exemplary configurations for connecting a battery to infusion pumps are shown. FIG. 12d depicts a battery and the wiring 209 that electrically connect the battery to the electrical circuitry of the infusion pump(s).

FIGS. 12a and 12b depict a dedicated cover (housing) 60 for a button battery 50 (as was previously described herein). The battery is connected to the electrical components of the device via connectors, namely, cathode connectors 203 and an anode connector 205. As shown, the connectors are located, in some embodiments, on the principal flat surfaces (e.g., upper and/or lower flat surfaces) of the button battery and thus provide large contact areas. In some embodiments, the dedicated cover 64 also includes a selective membrane 62 (also referred to as "semi permeable membrane" or "breathable membrane"). The dedicated cover 64 isolates and protects the battery, and possibly other components of the infusion pump, from the environment. As the battery may be located in part of the of the infusion pump, e.g., in the cradle, the disposable part and/or in the reusable part, the insulation cover may be made an integral part of these components as shown, for example, in FIGS. 7a to 7d.

The selective membrane 62 has a selective permeability. It thus protects the battery from the entrance of harmful materials such as water and other liquids, but enables oxygen transfer to the battery. Oxygen transfer to the battery's cathode prior to activating the infusion pump is prevented by a sealing mechanism, e.g., a seal 61. The seal can be placed on the selective membrane as shown in FIG. 12a, or it may be left directly on the battery as provided by the manufacturer as shown in FIG. 12b. When the seal is attached directly to the battery, an opening 65 to enable access to the sealing mechanism is left in the cover so that the seal's tab, for example, can be pulled to lift the seal.

When the battery is included, in some embodiments, within the disposable part or within the cradle, there is no need for battery replacement. Thus, the battery 50 can be soldered, or otherwise attached, during the pump manufacturing process to the electrical circuit through a set of wires 209 to avoid inadvertent disconnections. In some embodiments, the battery may be connected to the electrical circuit using a high contact area connector. For example, when a connection area between the battery's cathode and the connector, is more than 10 mm$^2$, e.g., between 18 mm$^2$ and 25 mm$^2$, the service life of the battery is significantly increased. The connection area may be increased by applying multiple standard connections, a grid of wires, a perforated plate or any other mechanism to electrically connect the battery without adversely affecting air ingress.

FIG. 12c shows a single connection 203 to the battery cathode 53. FIG. 12d shows more than one connection, for example three (3) connections 203, which can substantially increase the battery's service life. The connection can be to the same wire (not shown), or each connection can be associated with a separated wire 209. There may be fewer connections in circumstances where the contact area is sufficiently large, e.g., greater than 15 mm$^2$. It will be appreciated that for the purpose of connecting the battery to activate the electrical components of the infusion pump, the anode side 54 of the battery also has to be electrically connected.

Figure 12E:
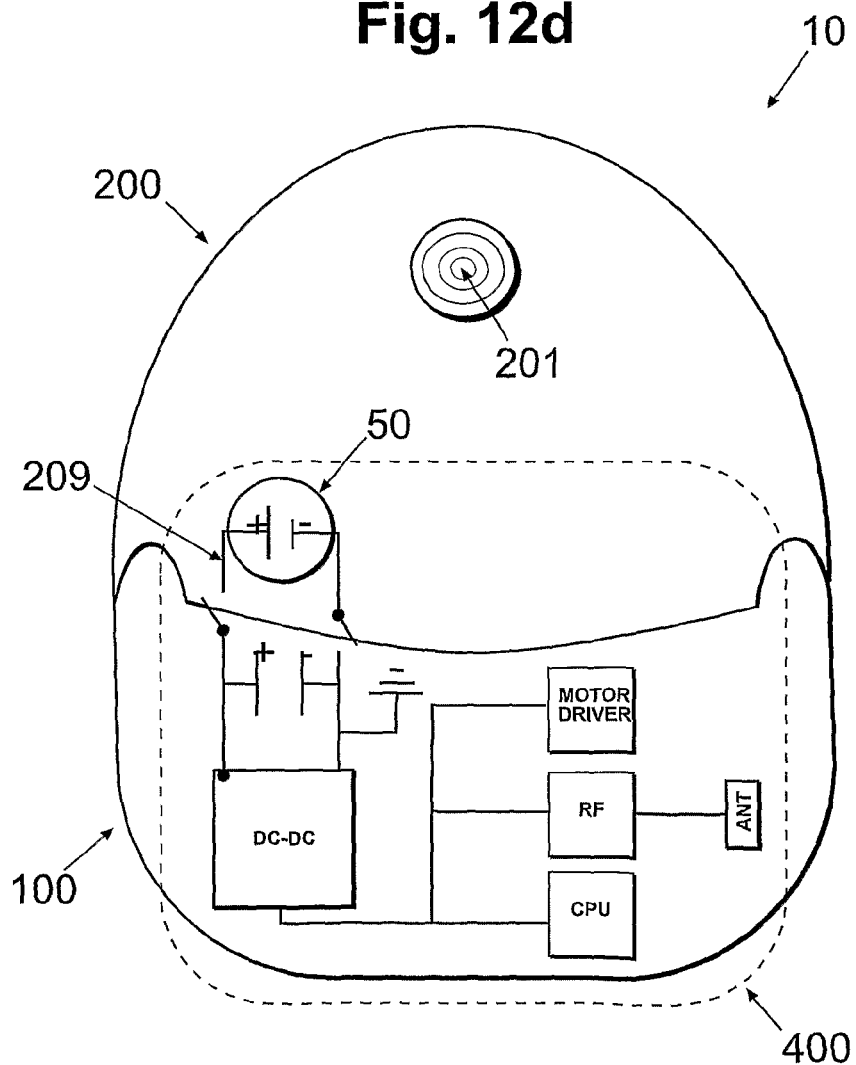

Referring to FIG. 12e, a schematic diagram, including the electrical arrangement, of an exemplary embodiment of a disposable 200 and reusable 100 parts of an infusion device 10 attached to each other is shown. In some embodiments, when these two parts are attached to each other the electrical circuit 400 is electrically closed once the battery 50 is connected to the other components of the electrical circuit. The battery may be soldered to wires 209 as shown, for example, in FIG. 12d. In some embodiments the battery may be pressed against connectors to enable electrical coupling with other electronics of the infusion device.

Although particular embodiments have been disclosed herein in detail, this has been done by way of example for purposes of illustration only, and is not intended to be limiting with respect to the scope of the appended exemplary claims, which follow. In particular, it is contemplated that various substitutions, alterations, and modifications may be made without departing from the spirit and scope of the invention as defined by the claims. Any and all of the foregoing patents, applications, and publications referenced in this specification are hereby incorporated by reference herein in their entireties. Other aspects, advantages, and modifications are considered to be within the scope of the following claims. The claims presented are representative of the inventions disclosed herein. Other, unclaimed inventions are also contemplated.

What is claimed is:

1. A portable ambulatory therapeutic fluid dispensing device for infusing a therapeutic fluid into a body of a user and optionally for sensing an analyte within the body, the device comprising a device housing including a disposable part housing and a separate reusable part housing connectable to the disposable part housing;
wherein the disposable part housing comprises:
a reservoir for containing a therapeutic fluid;
a source of energy to energize the device, the source of energy comprising at least one electrochemical cell configured to produce electrical energy upon exposure of the cell to air; and
a seal to prevent exposure of the at least one cell to air when the source of energy is not in use and configured to expose the at least one cell to air prior to energizing the device;
wherein the reusable part housing comprises:
at least a portion of a driving mechanism; and
a processor;
wherein the device housing has at least one air vent opening configured to expose the source of energy to air, and a second seal to prevent entry of air into at least one of the disposable part housing and the reusable part housing through the at least one air vent opening when the device is not in operation; and
wherein the device is operable upon connecting the disposable part housing and the reusable part housing such that the source of energy is exposed to air through the vent and electrical connectivity occurs between the source of energy and the at least a portion of the driving mechanism and the processor.

2. The device of claim 1, wherein the disposable part housing includes an opening for providing access to a tab associated with the seal, wherein the tab is configured to remove the seal resulting in the exposure of the at least one cell to the air.

3. The device of claim 1, wherein the reusable part housing includes a semi-permeable membrane within and/or adjacent the at least one air vent opening, and wherein the semi-permeable membrane allows entry of air into at least one of the disposable part housing and the reusable part housing and substantially prevents entry of at least some other materials into at least one of the disposable part housing and the reusable part housing.

4. The device of claim 3, wherein the at least some other materials include at least one of water and other liquids.

5. The device of claim 1, further comprising a sensor for sensing a bodily analyte level.

6. The device of claim 1, wherein the seal is secured to at least one surface of the source of energy through which air comes in contact with air-reactive parts of the source of energy.

7. The device of claim 1, wherein the seal includes a removable tab such that upon removal of the tab, the at least one cell of the source of energy is exposed to air.

8. The fluid dispensing device of claim 1, wherein the at least one cell includes at least one Zinc-Air cell.

9. The fluid dispensing device of claim 1, wherein the source of energy is configured as a button battery.

10. The device of claim 1, wherein the second seal substantially covers a semi-permeable membrane to substantially prevent entry of air via the at least one air vent opening into at least one of the disposable part housing and the reusable part housing.

11. The device of claim 1, wherein the disposable part housing comprises:
a dedicated energy source cover to retain at least the energy source; and
at least one second housing, wherein the at least one second housing is configured to receive and retain the dedicated energy source cover.

12. The device of claim 1, wherein the portion of the disposable part housing retaining the source of energy is integrally formed around the source of energy such that the source of energy cannot be removed.

13. The device of claim 1, wherein the source of energy includes a volume of less than or about 3 $cm^3$.

14. The device of claim 1, wherein at least one of the housings includes a thickness of less than or about 15 mm.

15. The device of claim 1, wherein the reusable part housing further comprises a capacitor for temporarily storing a charge from the source of energy during a first time interval and discharging the stored charge for activating the driving mechanism during a second time interval, and wherein the first time interval is longer than the second time interval.

16. The device of claim 15, wherein the first time interval is at least about 20 times longer than the second time interval.

17. The device of claim 15, wherein the first time interval is about 50 times longer than the second time interval.

18. The device of claim 15, wherein the first time interval overlaps, at least in part, the second time interval.

19. The device of claim 1, wherein the source of energy is recyclable and/or safely disposable in a non-biohazards container.

20. The device of claim 1, wherein the source of energy comprises at least one of: non-toxic materials, non-overly reactive materials and non-flammable materials.

21. The device of claim 1, wherein the at least one vent is provided on the disposable part housing.

22. A portable fluid dispensing device for infusing a fluid into a body of a user and optionally for sensing a bodily analyte, the device comprising:
a dispensing unit comprising a reservoir, a pump, and a first housing for housing the reservoir and the pump; and
a separate cradle unit connectable to the dispensing unit, the cradle unit comprising:
a second housing for securing the dispensing unit to the body of the user;
a source of energy to energize the dispensing unit, the source of energy comprising at least one electrochemical cell for producing electrical energy upon exposure of the cell to air;
at least one vent to expose the source of energy to air;
a seal for substantially preventing exposure of the at least one electrochemical cell to air when the source of energy is not in use and for exposing the at least one cell to air prior to energizing the dispensing unit with the source of energy;
a semi-permeable membrane placed within and/or adjacent the at least one vent, wherein the semi-permeable membrane is configured for entry of air into the cradle unit and configured for substantially preventing entry of at least some other materials into the cradle unit,
wherein the dispensing unit is operable upon connection to the cradle unit via establishment of electrical communication between the source of energy and the dispensing unit.

23. The device of claim 22, wherein a portion of the cradle unit retaining the source of energy is integrally formed around the energy source such that the energy source cannot be removed.

24. The device of claim 22, wherein the at least one electrochemical cell includes at least one Zinc-Air cell.

* * * * *